(12) United States Patent
Betts et al.

(10) Patent No.: US 10,619,186 B2
(45) Date of Patent: *Apr. 14, 2020

(54) METHODS AND COMPOSITIONS FOR LIBRARY NORMALIZATION

(71) Applicant: Cellular Research, Inc., Menlo Park, CA (US)

(72) Inventors: Craig Betts, Menlo Park, CA (US); Glenn Fu, Menlo Park, CA (US)

(73) Assignee: Cellular Research, Inc., Menlo Park, CA (US)

( * ) Notice: Subject to any disclaimer, the term of this patent is extended or adjusted under 35 U.S.C. 154(b) by 110 days.

This patent is subject to a terminal disclaimer.

(21) Appl. No.: 15/260,106

(22) Filed: Sep. 8, 2016

(65) Prior Publication Data

US 2017/0073730 A1    Mar. 16, 2017

Related U.S. Application Data

(60) Provisional application No. 62/217,220, filed on Sep. 11, 2015.

(51) Int. Cl.
*C12P 19/34* (2006.01)
*C12Q 1/6806* (2018.01)
*C12N 15/10* (2006.01)

(52) U.S. Cl.
CPC ....... *C12Q 1/6806* (2013.01); *C12N 15/1093* (2013.01); *C12N 15/1096* (2013.01); *C12Q 2525/191* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS

| | | |
|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |

(Continued)

FOREIGN PATENT DOCUMENTS

| | | |
|---|---|---|
| CN | 109791157 | 5/2019 |
| CN | 110382708 | 10/2019 |

(Continued)

OTHER PUBLICATIONS

Soares et al., Construction and characterization of a normalized cDNA library. Proc. Natl. Acad. Sci, USA, 91, 9228-9232, 1994.*

(Continued)

*Primary Examiner* — Frank W Lu

(74) *Attorney, Agent, or Firm* — Sheppard, Mullin, Richter & Hampton LLP

(57) ABSTRACT

The disclosure provides for methods, compositions, and kits for normalizing nucleic acid libraries, for example sequencing libraries.

27 Claims, 8 Drawing Sheets

(56) References Cited

U.S. PATENT DOCUMENTS

| | | |
|---|---|---|
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,830,712 A | 11/1998 | Rampersad et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 * | 3/2001 | Lin .................. C12N 15/1093 435/15 |
| 6,235,475 B1 | 5/2001 | Brenner et al. |
| 6,268,152 B1 | 7/2001 | Fodor et al. |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1 | 12/2006 | Sloge |
| 7,393,665 B2 | 7/2008 | Brenner |
| 7,407,757 B2 | 8/2008 | Brenner |
| 7,424,368 B2 | 9/2008 | Huang et al. |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,228,229 B2 | 1/2016 | Olson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,567,646 B2 | 2/2017 | Fan et al. |
| 10,047,394 B2 | 8/2018 | Fodor et al. |
| 10,059,991 B2 | 8/2018 | Fodor et al. |
| 10,202,641 B2 | 2/2019 | Shum et al. |
| 10,202,646 B2 | 2/2019 | Fodor et al. |
| 10,208,356 B1 | 2/2019 | Fan et al. |
| 10,246,703 B2 | 4/2019 | Church et al. |
| 10,253,375 B1 | 4/2019 | Fan et al. |
| 10,301,677 B2 | 5/2019 | Shum et al. |
| 10,338,066 B2 | 7/2019 | Fan et al. |
| 10,392,661 B2 | 8/2019 | Fodor et al. |
| 2002/0019005 A1 * | 2/2002 | Kamb ................ C12N 15/1086 435/6.14 |
| 2002/0072058 A1 | 6/2002 | Voelker et al. |
| 2002/0168665 A1 | 11/2002 | Okawa |
| 2002/0192687 A1 | 12/2002 | Mirkin et al. |
| 2003/0003490 A1 | 1/2003 | Fan et al. |
| 2003/0049616 A1 | 3/2003 | Brenner et al. |
| 2003/0082818 A1 | 5/2003 | Bahnson et al. |
| 2003/0104436 A1 | 6/2003 | Morris et al. |
| 2003/0175908 A1 | 9/2003 | Linnarson |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0170373 A1 | 8/2005 | Monforte |
| 2005/0175993 A1 * | 8/2005 | Wei .................. C12N 15/1096 435/6.16 |
| 2005/0214825 A1 | 9/2005 | Stuelpnagel |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0041385 A1 | 2/2006 | Bauer |
| 2006/0073506 A1 | 4/2006 | Christians et al. |
| 2006/0211030 A1 | 9/2006 | Brenner |
| 2006/0263709 A1 | 11/2006 | Matsumura et al. |
| 2006/0263789 A1 | 11/2006 | Kincaid |
| 2007/0020640 A1 | 1/2007 | Mccloskey et al. |
| 2007/0065823 A1 | 3/2007 | Dressman et al. |
| 2007/0117134 A1 | 5/2007 | Kou |
| 2007/0172873 A1 | 7/2007 | Brenner et al. |
| 2007/0178478 A1 | 8/2007 | Dhallan et al. |
| 2008/0070303 A1 | 3/2008 | West et al. |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0053698 A1 * | 2/2009 | Hayashida ......... C12N 15/1072 435/6.14 |
| 2009/0061513 A1 | 3/2009 | Andersson et al. |
| 2009/0105959 A1 | 4/2009 | Braverman et al. |

(56) References Cited

U.S. PATENT DOCUMENTS

| | | |
|---|---|---|
| 2009/0137407 A1 | 5/2009 | Church et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0298709 A1 | 12/2009 | Ma |
| 2010/0069250 A1 | 3/2010 | White, III |
| 2010/0105049 A1 | 4/2010 | Ehrich et al. |
| 2010/0105886 A1 | 4/2010 | Woudenberg et al. |
| 2010/0120098 A1 | 5/2010 | Grunenwald et al. |
| 2010/0120630 A1 | 5/2010 | Huang et al. |
| 2010/0255471 A1 | 10/2010 | Clarke |
| 2010/0291666 A1 | 11/2010 | Collier et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0040843 A1 | 2/2012 | Ducree et al. |
| 2012/0045844 A1 | 2/2012 | Rothberg et al. |
| 2012/0065081 A1 | 3/2012 | Chee |
| 2012/0071331 A1 | 3/2012 | Casbon |
| 2012/0156675 A1 | 6/2012 | Lueerssen et al. |
| 2012/0163681 A1 | 6/2012 | Lohse |
| 2012/0173159 A1 | 7/2012 | Davey et al. |
| 2012/0190020 A1 | 7/2012 | Oliphant et al. |
| 2012/0220022 A1 | 8/2012 | Ehrlich et al. |
| 2012/0220494 A1 | 8/2012 | Samuels |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0057799 A1 | 2/2014 | Johnson et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206547 A1 | 7/2014 | Wang |
| 2014/0216128 A1 | 8/2014 | Neat |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1 | 1/2015 | Hindson et al. |
| 2015/0066385 A1 | 3/2015 | Schnall-levin et al. |
| 2015/0099673 A1 | 4/2015 | Fodor et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0211050 A1 | 7/2015 | Iafrate et al. |
| 2015/0225778 A1 | 8/2015 | Hindson et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0329852 A1 | 11/2015 | Nolan |
| 2015/0376609 A1 | 12/2015 | Hindson et al. |
| 2016/0010151 A1 | 1/2016 | Fan et al. |
| 2016/0017320 A1 | 1/2016 | Wang et al. |
| 2016/0026758 A1 | 1/2016 | Jabara et al. |
| 2016/0055632 A1 | 2/2016 | Fu et al. |
| 2016/0068889 A1 | 3/2016 | Gole et al. |
| 2016/0145683 A1 | 5/2016 | Fan et al. |
| 2016/0222378 A1 | 8/2016 | Fodor et al. |
| 2016/0244828 A1 | 8/2016 | Mason |
| 2016/0253584 A1 | 9/2016 | Fodor et al. |
| 2016/0257993 A1 | 9/2016 | Fu et al. |
| 2016/0265069 A1 | 9/2016 | Fan et al. |
| 2016/0289669 A1 | 10/2016 | Fan et al. |
| 2016/0289670 A1 | 10/2016 | Samuels et al. |
| 2016/0289740 A1 | 10/2016 | Fu et al. |
| 2016/0312276 A1 | 10/2016 | Fu et al. |
| 2016/0320720 A1 | 11/2016 | Fan et al. |
| 2016/0326584 A1 | 11/2016 | Fodor et al. |
| 2016/0376583 A1 | 12/2016 | Fodor et al. |
| 2016/0376648 A1 | 12/2016 | Fodor et al. |
| 2017/0154421 A1 | 6/2017 | Fu et al. |
| 2017/0342484 A1 | 11/2017 | Shum et al. |
| 2018/0208975 A1 | 7/2018 | Peterson et al. |
| 2018/0216174 A1 | 8/2018 | Shum et al. |
| 2018/0251825 A1 | 9/2018 | Stoeckius et al. |
| 2019/0040474 A1 | 2/2019 | Fan et al. |
| 2019/0085412 A1 | 3/2019 | Fan et al. |
| 2019/0100798 A1 | 4/2019 | Fodor et al. |
| 2019/0119726 A1 | 4/2019 | Shum et al. |
| 2019/0292592 A1 | 9/2019 | Shum et al. |
| 2019/0338278 A1 | 11/2019 | Shum et al. |
| 2019/0338357 A1 | 11/2019 | Fan et al. |

FOREIGN PATENT DOCUMENTS

| | | |
|---|---|---|
| DE | 102008025656 | 12/2009 |
| EP | 0 799 897 | 10/1997 |
| EP | 1 473 080 | 11/2004 |
| EP | 1 647 600 | 4/2006 |
| EP | 1 845 160 | 10/2007 |
| EP | 2036989 | 3/2009 |
| EP | 2 623 613 | 8/2013 |
| EP | 2 805 769 | 11/2014 |
| EP | 3480321 | 5/2019 |
| EP | 3347465 | 6/2019 |
| EP | 3516400 | 7/2019 |
| EP | 3577232 | 12/2019 |
| GB | 2293238 | 3/1996 |
| GB | 2293238 A | 3/1996 |
| WO | WO 89/01050 | 2/1989 |
| WO | WO1996024061 | 8/1996 |
| WO | WO 99/15702 | 4/1999 |
| WO | WO 00/58516 | 10/2000 |
| WO | WO 02/056014 | 7/2002 |
| WO | WO 02/070684 | 9/2002 |
| WO | WO 04/017374 | 2/2004 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO 06/071776 | 7/2006 |
| WO | WO 06/102264 | 9/2006 |

(56) References Cited

FOREIGN PATENT DOCUMENTS

| | | |
|---|---|---|
| WO | WO 07/087310 | 8/2007 |
| WO | WO 07/087312 | 8/2007 |
| WO | WO 08/096318 | 8/2008 |
| WO | WO 09/148560 | 12/2009 |
| WO | WO 09/152928 | 12/2009 |
| WO | WO 10/117620 | 10/2010 |
| WO | WO 11/123246 | 10/2011 |
| WO | WO 11/143659 | 11/2011 |
| WO | WO 11/155833 | 12/2011 |
| WO | WO 12/038839 | 3/2012 |
| WO | WO 12/042374 | 4/2012 |
| WO | WO 12/047297 | 4/2012 |
| WO | WO 12/048341 | 4/2012 |
| WO | WO 12/083225 | 6/2012 |
| WO | WO 12/108864 | 8/2012 |
| WO | WO2012103154 | 8/2012 |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/162267 | 11/2012 |
| WO | WO 13/019075 | 2/2013 |
| WO | WO 13/117595 | 8/2013 |
| WO | WO 13/130674 | 9/2013 |
| WO | WO 13/173394 | 11/2013 |
| WO | WO 13/176767 | 11/2013 |
| WO | WO 13/177206 | 11/2013 |
| WO | WO 13/188831 | 12/2013 |
| WO | WO 13/188872 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO 14/028537 | 2/2014 |
| WO | WO2014065756 | 5/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO 14/144495 | 9/2014 |
| WO | WO 14/201273 | 12/2014 |
| WO | WO 14/210353 | 12/2014 |
| WO | WO2014200767 | 12/2014 |
| WO | WO2014204939 | 12/2014 |
| WO | WO2014210353 | 12/2014 |
| WO | WO 15/002908 | 1/2015 |
| WO | WO 15/031691 | 3/2015 |
| WO | WO 14/071361 | 5/2015 |
| WO | WO 15/103339 | 7/2015 |
| WO | WO 15/117163 | 8/2015 |
| WO | WO 15/200869 | 12/2015 |
| WO | WO2016044227 | 3/2016 |
| WO | WO2016061517 | 4/2016 |
| WO | WO2016118915 | 7/2016 |
| WO | WO2016160965 | 8/2016 |
| WO | WO2016149418 | 9/2016 |
| WO | WO2016160844 | 10/2016 |
| WO | WO2016191272 | 12/2016 |
| WO | WO2017079593 | 5/2017 |
| WO | WO2018031631 | 2/2018 |
| WO | WO2018058073 | 3/2018 |
| WO | WO2018226293 | 12/2018 |
| WO | WO2013137737 | 9/2019 |
| WO | WO2019213237 | 11/2019 |
| WO | WO2019213294 | 11/2019 |

OTHER PUBLICATIONS

Achim et al., May 2015, High-throughput spatial mapping of single-cell RNA-seq data to tissue of origin. Nature Biotechnology, 33(5):503-511.
Alkan et al., Oct. 2009, Personalized copy number and segmental duplication maps using next-generation sequencing. Nat Genet., 41(10):1061-1067.
Anderson, Feb. 11, 2014, Study describes RNA sequencing applications for molecular indexing methods, genomeweb.com, 5 pp.
Ansorge, 2009, Next-generation DNA sequencing techniques. New Biotechnology, 25(4):195-203.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http://bionumbers.hms.harvard.edu/KeyNumbers/aspx, 4 pp.
Bioscribe, Feb. 5, 2015, Massively parallel sequencing technology for single-cell gene expression published (press release), 3 pp.
Blainey, May 2013, The future is now: single-cell genomics of bacteria and archaea, FEMS Microbiol Rev., 37(3):407-427.
Bonaldo et al., Sep. 1996, Normalization and subtraction: two approaches to facilitate gene discovery. Genome Res., 6(9):791-806.
Braha et al., 2000, Simultaneous stochastic sensing of divalent metal ions. Nature Biotechnology, 18:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brisco et al., Jun. 25, 2012, Quantification of RNA integrity and its use for measurement of transcript number, Nucleic Acids Research, 40(18):e144.
Brodin et al., 2015, Challenges with using primer IDs to improve accuracy of next generation sequencing, 19(3):1-12.
Butkus, Feb. 6, 2014, Cellular research set to launch first gene expression platform using 'molecular indexing' technology, genomeweb.com, 5 pp.
Cai, Mar. 2013, Turning single cells in microarrays by super-resolution bar-coding, Brief Funct Genomics, 12(2):75-80.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castellarnau et al., Jan. 2015, Stochastic particle barcoding for single-cell tracking and multiparametric analysis, Small, 11(4):489-498.
Castle et al., Apr. 16, 2010, DNA copy number, including telomeres and mitochondria, assayed using next-generation sequencing. BMC Genomics, 11:244. doi: 10.1186/1471-2164-11-244.
Chamberlain et al., Dec. 9, 1988, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.
Church et al., 1988, Multiplex DNA sequencing. Science, 240:185-188.

(56) References Cited

OTHER PUBLICATIONS

Costello et al., Apr. 1, 2013, Discovery and characterization of artefactual mutations in deep coverage targeted capture sequencing data due to oxidative DNA damage during sample preparation. Nucleic Acids Res, 41(6):e67.
Cox. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Daines et al., Aug. 2009, High-throughput multiplex sequencing to discover copy number variants in *Drosophila*. Genetics, 182(4):935-941.
Dalerba et al., 2011, Single-cell dissection of transcriptional heterogeneity in human colon tumors, Nat Biotechnol., 29(12):1120-1127 and Supplementary Material.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.
De Saizieu et al., 1998, Bacterial transcript imaging by hybridization of total RNA to oligonucleotide arrays. Nature Biotechnology, 16:45-48.
Dirks et al., Oct. 26, 2004, Triggered amplification by hybridization chain reaction., Proc Natl Acad Sci U S A, 101(43), 15275-15278.
Fan et al., Feb. 6, 2015, Combinatorial labeling of single cells for gene expression cytometry. Science, 347(6222):1258367-8.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Jul. 19, 2012, Non-invasive prenatal measurement of the fetal genome. Nature, 487(7407):320-324.
Fan Nov. 2010, Molecular counting: from noninvasive prenatal diagnostics to whole-genome haplotyping, doctoral dissertation, Stanford University, 185 pp.
Feldhaus et al., Jan. 15, 2000, Oligonucleotide-conjugated beads for transdominant genetic experiments, Nucleic Acids Res., 28(2):534-543.
Fox-Walsh et al., Oct. 2011, A multiplex RNA-seq strategy to profile poly(A+) RNA: application to analysis of transcription response and 3' end formation., Genomics, 98(4),266-721.
Fu et al., Mar. 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Gong et al., 2010, Massively parallel detection of gene expression in single cells using subnanolitre wells, Lab Chip, 10:2334-2337.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.
Gundry et al., Mar. 2012, Direct, genome-wide assessment of DNA mutations in single cells. Nucleic Acids Res., 40(5):2032-40.

Hacia et al., 1999, Determination of ancestral alleles for human single-nucleotide polymorphisms using high-density oligonucleotide arrays. Nature Genetics, 22:164-167.
Haff, 1994, Improved quantitative PCR using nested primers, PCR Methods and Applications, 3:332-337.
Hamady et al., Mar. 2008, Error-correcting barcoded primers for pyrosequencing hundreds of samples in multiplex. Nat Methods, 5(3):235-237.
Harrington et al.,2009, Cross-sectional characterization of HIV-1 env compartmentalization in cerebrospinal fluid over the full disease course, AIDS, 23(8) 907-915.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.
Hug et al., 2003, Measure of the number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Junker et al., May 21, 2015, Single-cell transcriptomics enters the age of mass production, Molecular Cell, 58:563-564.
Kanagawa, 2003, Bias and artifacts in multitemplate polymerase chain reactions (PCR), Journal of Bioscience and Bioengineering, 96(4):317-323.
Kebschull et al., Jul. 17, 2015, Sources of PCR-induced distortions in high-throughput sequencing data sets, Nucleic Acids Research, 15 pp.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kim et al., Jun. 8, 2007, Polony multiplex analysis of gene expression (PMAGE) in mouse hypertrophic cardiomyopathy, Science, 316(5830):1481-1484.
Kinde et al., Jun. 7, 2011, Detection and quantification of rare mutations with massively parallel sequencing, Proc. Natl Acad Sci, 108(23):9530-0535.
Kivioja et al., Jan. 2012, Counting absolute numbers of molecules using unique molecular identifiers. Nature Methods, 9(1):72-76.
Klein et al., May 21, 2015, Droplet barcoding for single-cell transcriptomics applied to embryonic stem cells, Cell, 161:1187-1201.
Koboldt et al., Sep. 1, 2009, VarScan: variant detection in massively parallel sequencing of individual and pooled samples. Bioinformatics. 25(17):2283-2285.
Kolodziejczyk et al., May 21, 2015, The technology and biology of single-cell RNA sequencing, Molecular Cell, 58:610-620.
Konig et al., Jul. 2010, iCLIP reveals the function of hnRNAP particles in splicing at individual nucleotide resolution, Nature Structural & Molecular Biology, 17(7):909-916.

(56) References Cited

OTHER PUBLICATIONS

Kotake et al., 1996, A simple nested RT-PCR method for quantitation of the relative amounts of multiple cytokine mRNAs in small tissue samples, Journal of Immunological Methods, 199:193-203.
Kurimoto et al., Mar. 17, 2006, An improved single-cell cDNA amplification method for efficient high-density oligonucleotide microarray analysis, Nucleic Acids Res., 34(5):e42.
Lamble et al., Nov. 20, 2013, Improved workflows for high throughput library preparation using the transposome-based nextera system, BMC Biotechnology, 13(1):104.
Larson et al., Nov. 2009, A single molecule view of gene expression. Trends Cell Biol. 19(11):630-637.
Leamon et al., Nov. 2003, A massively parallel PicoTiterPlate based platform for discrete picoliter-scale polymerase chain reactions, Electrophoresis, 24(21):3769-3777.
Lee et al., 2010, Large-scale arrays of picolitre chambers for single-cell analysis of large cell populations, Lab Chip, 10:2952-2958.
Lee et al., Mar. 21, 2014, Highly multiplexed subcellular RNA sequencing in situ. Science. 343(6177):1360-1363.
Liu et al., Single-cell transcriptome sequencing: recent advances and remaining challenges, F1000Research 2016, 5(F1000 Faculty Rev):182, 9 pp.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods. 11(2):190-196.
Lucito et al., 1996, Representational Oligonucleotide Microarray Analysis: A High-Resolution Method to Detect Genome Copy Number Variation. Genome Research, 13: 2291-2305.
Maamar et al., 2007, Noise in Gene Expression Determines Cell Fate in Bacillus subtilis. Science, 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Makrigiorgos et al., Sep. 2002, a PCR-Based amplification method retaining quantities difference between two complex genomes. Nature Biotech, 20(9):936-939.
Marcus et a., 2006, Microfluidic single-cell mRNA isolation and analysis, Ana. Chem. 78:3084-3089.
Margulies et al., Sep. 15, 2005 Genome sequencing in microfabricated high-density picolitre reactors, Nature, 437:376-380.
Martinez et al., Jul. 2012, A microfluidic approach to encapsulate living cells in uniform alginate hydrogel microparticles, Macromol. Biosci, 12(7):946-951.
McCloskey et al., Dec. 2007, Encoding PCR products with batch-stamps and barcodes. Biochem Genet. 45(11-12):761-767.
Medvedev et al., Nov. 2010, Detecting copy number variation with mated short reads. Genome Res. 20(11):1613-1622.
Mei et al., Mar. 22, 2010, Identification of recurrent regions of Copy-Number Variants across multiple individuals. BMC Bioinformatics. 11:147.
Merriam-Webster, definition of associate,: http://www.merriam-webster.com/dictionary/associate, accessed Apr. 5, 2016.
Miller et al., 2006, Directed evolution by in vitro compartmentalization, Nature Methods, 3:561-570.
Miner et al., 2004, Molecular barcodes detect redundancy and contamination in hairpin-bisulfite PCR, Nucleic Acids Research, 32(17):e135.
Mortazavi et al., 2008, Mapping and quantifying mammalian transcriptomes by RNA-Seq. Nat. Methods. 5:621-628.
Nadai et al., 2008, Protocol for nearly full-length sequencing of HIV-1 RNA from plasma, PLoS One, 3(1):e1420.

Nagai et al., 2001, Development of a microchamber array for picoleter PCR, Anal. Chem., 73:1043-1047.
Navin et al., 2015, The first five years of single-cell cancer genomics and beyond, Genome Research, 25(10):1499-1507.
Newell et al., Jan. 27, 2012, Cytometry by time-of-flight shows combinatorial cytokine expression and virus-specific cell niches within a continuum of CD8+ T cell phenotypes. Immunity. 36(1):142-152.
Novak et al., Jan. 20, 2011, Single-cell multiplex gene detection and sequencing with microfluidically generated agarose emulsions, Angew Chem Int Ed Engl., 50(2):390-395.
Ogino et al., Nov. 2002, Quantification of PCR bias caused by a single nucleotide polymorphism in SMN gene dosage analysis. J Mol Diagn. 4(4):185-190.
Parameswaran et al., 2007, A pyrosequencing-tailored nucleotide barcode design unveils opportunities for large-scale sample multiplexing. Nucleic Acids Res. 35(19):e130.
Park et al., May 2010, Discovery of common Asian copy number variants using integrated high-resolution array CGH and massively parallel DNA sequencing. Nat Genet. 42(5):400-405.
Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.
Picelli et al., Jul. 30, 2014, Tn5 transposase and tagmentation procedures for massively scaled sequencing projects, Genome Research 24(12):2033-2040.
Pihlak et al., 2008, Rapid genome sequencing with short universal tiling probes. Nature Biotechnology, 26:676-684.
Pinkel et al., 2005, Comparative Genomic Hybridization. Annual Review of Genomics and Human Genetics, 6:331-354.
Pleasance et al., Jan. 14, 2010, A small-cell lung cancer genome with complex signatures of tobacco exposure. Nature. 463(7278):184-190.
Plessy et al., Feb. 2013, Population transcriptomics with single-cell resolution: a new field made possible by microfluidics: a technology for high throughput transcript counting and data-driven definition of cell types, Bioessays, 35(2):131-140.
Qiu et al., Oct. 2003, DNA sequence-based "bar codes" for tracking the origins of expressed sequence tags from a maize cDNA library constructed using multiple mRNA sources. Plant Physiol. 133(2):475-481.
Rajeevan et al., Oct. 2003, Global amplification of sense RNA: a novel method to replicate and archive mRNA for gene expression analysis, Genomics, 82(4):491-497.
Roche Diagnostics GmbH, 2006, Genome Sequencer 20 System: First to the Finish (product brochure), 40 pp.
Sasagawa et al., 2013, Quartz-Seq: a highly reproducible and sensitive single-cell RNA sequencing method, reveals non-genetic gene-expression heterogeneity. Genome Biology, 14:R31.
Sasuga et al., Dec. 2008, Single-cell chemical lysis method for analyses of intracellular molecules using an array of picoliter-scale microwells, Anal Chem, 80(23):9141-9149.
Satija et al., May 2015, Spatial reconstruction of single-cell gene expression data. Nature Biotechnology, 33(5):495-508.
Schmitt et al., Sep. 4, 2012, Detection of ultra-rare mutations by next-generation sequencing. Proc Natl Acad Sci U S A. 109(36):14508-14513.
Sebat et al., 2004, Large-Scale Copy Number Polymorphism in the Human Genome. Science, 305:525-528.
Shalek et al., Jun. 13, 2013, Single-cell transcriptomics reveals bimodality in expression and splicing in immune cells. Nature. 498(7453):236-240.
Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.
Shoemaker et al., 1996, Quantitative phenotypic analysis of yeast deletion mutants using a highly parallel molecular bar-coding strategy. Nature Genetics, 14:450-456.
Simpson et al., Feb. 15, 2010, Copy number variant detection in inbred strains from short read sequence data. Bioinformatics. 26(4):565-567.

(56) References Cited

OTHER PUBLICATIONS

Smith et al., 2010, Highly-multiplexed barcode sequencing: an efficient method for parallel analysis of pooled samples. Nucleic Acids Research, 38(13):e142.
Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.
Speicher et al., Oct. 2005, The new cytogenetics: blurring the boundaries with molecular biology, Nature Reviews Genetics, 6(10):782-792.
Stratagene 1998 Catalog, Gene Characterization Kits, p. 39.
Takahashi et al., Mar. 2006, Novel technique of quantitative nested real-time PCR assay for *Mycobacterium tuberculosis* DNA, Journal of Clinical Microbiology, 44(3):1029-1039.
Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.
Taudien et al., Apr. 19, 2010, Haplotyping and copy number estimation of the highly polymorphic human beta-defensin locus on 8p23 by 454 amplicon sequencing. BMC Genomics. 11:252.
The Tibbs Times, UNC bioscience newsletter, Apr. 2010, 17 pp.
Tomaz et al., Aug. 2010, Differential methylation as a cause of allele dropout at the imprinted GNAS locus. Genet Test Mol Biomarkers. 14(4):455-460.
Treutlein et al., May 15, 2014, Reconstructing lineage hierarchies of the distal lung epithelium using single-cell RNA-seq. Nature. 509(7500):371-375.
Vandesompele et al., Jun. 18, 2002, Accurate normalization of real-time quantitative RT-PCR data by geometric averaging of multiple internal control genes, Genome Biology, 3(7).
Velculescu et al., 1995, Serial Analysis of Gene Expression. Science, 270:484-487.
Velculescu et al., 1997, Characterization of the Yeast Transcriptome. Cell, 88:243-251.
Vogelstein et al., 1999, Digital PCR. Proc. Natl. Acad. Sci., 96(16):9236-9241.
Walker et al., Jan. 1, 1992, Isothermal in vitro amplification of DNA by a restriction enzyme/DNA polymerase system. Proc Natl Acad Sci U S A., 89(1):392-396.
Walsh et al., Jul. 13, 2010, Detection of inherited mutations for breast and ovarian cancer using genomic capture and massively parallel sequencing. Proc Natl Acad Sci U S A. 107(28):12629-12633.
Wang et al., 2009, RNA-Seq: a revolutionary tool for transcriptomics. Nature Reviews Genetics, 10:57-63.
Wang et al., May 21, 2015, Advances and applications of single-cell sequencing technologies, Molecular Cell, 58(4):598-609.
Wang et al., Oct. 2010, iCLIP predicts the dual splicing effects of TIA-RNA interactions, PLoS Biol, 8(10):e1000530.
Warren et al., Nov. 21, 2006, Transcription factor profiling in individual hematopoietic progenitors by digital RT-PCR, PNAS, 103(47):17807-17812.
Weber et al., Sep. 15, 2003, A real-time polymerase chain reaction assay for quantification of allele ratios and correction of amplification bias. Anal Biochem. 320(2):252-258.
Weiner et al., Apr. 2008, Kits and their unique role in molecular biology: a brief retrospective, BioTechniques, 44:701-704.
White et al., Aug. 23, 2011, High-throughput microfluidic single-cell RT-qPCR, PNAS, 108(34):13999-14004.
Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nano-gram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage. Genome Res. 19(9):1586-1592.
Zhang et al., Jun. 19, 2012, DNA-based hybridization chain reaction for amplified bioelectronic signal and ultrasensitive detection of proteins. Anal Chem., 84(12),5392-5399.
Zhang et al., Mar. 20, 2011, The impact of next-generation sequencing on genomics. J Genet Genomics. 38(3):95-109.
Zhao et al., 2005, Homozygous Deletions and Chromosome Amplifications in Human Lung Carcinomas Revealed by Single Nucleotide Polymorphism Array Analysis. Cancer Research, 65:5561-5570.
Zheng et al., Feb. 2016, Haplotyping germline and cancer genomes with high-throughput linked-read sequencing, Nature Biotechnology, 34(3):303-311.
Zhou et al., 2001, Counting alleles reveals a connection between chromosome 18q loss and vascular invasion. Nature Biotechnology, 19:78-81.
International Search Report and Written Opinion dated May 3, 2016 in PCT/US16/018354.
Office action dated Oct. 3, 2013 for U.S. Appl No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office action dated Jul. 20, 2016 for U.S. Appl. No. 14/281,706.
Office Action dated Oct. 11, 2016 in U.S. Appl. No. 15/224,460.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
International Search Report and Written Opinion dated Jun. 6, 2012 in PCT/US11/065291.
Restriction Requirement dated Mar. 15, 2016 in U.S. Appl. No. 14/381,488.
Office Action dated May 10, 2016 in U.S. Appl. No. 14/381,488.
Office Action dated Aug. 12, 2016 in U.S. Appl. No. 14/381,488.
International Search Report and Written Opinion dated Sep. 6, 2013 in PCT/US13/028103.
Second Office Action dated Jun. 6, 2016 in Chinese patent application No. 201380022187.9.
European search report and search opinion dated Jul. 17, 2015 for European patent application No. 13755319.4.
Examination report dated Jul. 12, 2016 in European patent application No. 13755319.4.
Search and Examination Report dated Aug. 6, 2014 for GB patent application No. 1408829.8.
Search and Examination Report dated Jan. 27, 2016 in GB patent application No. 1408829.8.

(56) References Cited

OTHER PUBLICATIONS

Examination Report dated Jun. 8, 2016 in GB patent application No. 1408829.8.
Search Report and Written Opinion dated Mar. 1, 2016 in Singapore patent application No. 1120140527W.
International search report and written opinion dated Aug. 16, 2013 for PCT/US2013/027891.
Extended European Search Report dated Dec. 15, 2015 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
Office action dated Aug. 17, 2016 for U.S. Appl. No. 14/800,526.
Office Action dated Oct. 25, 2016 in U.S. Appl. No. 14/872,337.
Office action dated Sep. 26, 2016 in U.S. Appl. No. 15/167,807.
International Search Report and Written Opinion dated Feb. 3, 2015 in PCT/US/14/053301.
Search and Examination Report dated Aug. 26, 2015 in GB patent application No. 1511591.8.
Examination Report dated Feb. 19, 2016 in Great Britain patent application No. GB1511591.8.
Examination Report dated Jun. 15, 2016 in Great Britain patent application No. GB1511591.8.
Office Action dated May 13, 2016 in U.S. Appl. No. 14/508,911.
International search report and written opinion dated Dec. 19, 2014 for PCT Application No. US2014/059542.
International Search Report and Written Opinion dated Jun. 20, 2016 in PCT/US16/14612.
International Search Report and Written Opinion dated Jun. 17, 2016 in PCT/US16/019962.
Written Opinion dated Jul. 5, 2016 in PCT/US16/019962.
Written Opinion dated Sep. 27, 2016 in PCT/US16/019962.
Invitation to Pay Additional Search Fees dated Jun. 2, 2016 in PCT/US16/019971.
International Search Report and Written Opinion dated Aug. 9, 2016 in PCT/US16/019971.
International Search Report and Written Opinion dated Jun. 9, 2016 in PCT/US16/022712.
International Search Report and Written Opinion dated Dec. 5, 2016 in PCT/US16/024783.
International Search Report and Written Opinion dated Sep. 28, 2016 in PCT/US16/028694.
International Search Report and Written Opinion dated Sep. 27, 2016 in PCT/US16/034473.
International search report and written opinion dated May 7, 2012 for PCT/IB2011/003160.
Notice of opposition dated Jul. 22, 2015 for European patent application No. 11810645.9.
Notice of opposition dated Jul. 9, 2015 for European patent application No. 11810645.9.
Bogdanova et al., Jan. 2008, Normalization of full-length enriched cDNA, Molecular Biosystems, 4(3):205.
Patanjali et al., Mar. 1991, Construction of a uniform-abundance (normalized) CNDA library, Proceedings of the National Academy of Sciences, 88(5):1943-1947.
Office Action dated Feb. 13, 2017 in U.S. Appl. No. 14/381,488.
Office Action dated Dec. 27, 2016 in Chinese patent application No. 201380022187.9.
Official Action dated Dec. 28, 2016 in Japanese patent application No. 2014-558975.
Combined Search and Examination Report dated Feb. 21, 2017 in GB patent application No. 1609740.4.
Office Action dated Jan. 19, 2017 in U.S. Appl. No. 15/055,445.
International Search Report and Written Opinion dated Jan. 31, 2017 in PCT/US16/050694.
Gu et al., 2016, Depletion of abundant sequences by hybridization (DSH): using Cas9 to remove unwanted high-abundance species in sequencing libraries and molecular counting applications, Genome Biology, 17:41, 13 pp.
Office Action dated Apr. 6, 2018 in U.S. Appl. No. 15/603,239.
International Search Report and Written Opinion dated Mar. 28, 2018 in patent application No. PCT/US2018/014385.
Peng et al., Mar. 11, 2016, Reducing amplification artifacts in high multiplex amplicon sequencing by using molecular barcodes, BMC Genomics, retrieved from the internet: url:http://bmcgenomics.biomedcentral.com/articles/0.1186/s12864-015-1806-8, 14 pages.
Office Action dated May 8, 2017 in U.S. Appl. No. 15/224,460.
Office Action dated Jul. 28, 2017 in U.S. Appl. No. 14/975,441.
Office Action dated Jun. 7, 2017 in U.S. Appl. No. 14/381,488.
Office Action dated Feb. 17, 2017 in Canadian patent application No. 2,865,575.
Fourth Office Action dated Jul. 14, 2017 in Chinese patent application No. 201380022187.9.
Written Opinion dated May 26, 2017 in Singapore patent application No. 11201405274W.
Examination Report dated Apr. 10, 2017 in European patent application No. 14761937.3.
Office Action dated Mar. 24, 2017 in U.S. Appl. No. 15/409,355.
International Search Report and Written Opinion dated Aug. 7, 2017 in PCT/US2017/034576.
Di Carlo et al., Dec. 1, 2008, Dynamic single-cell analysis for quantitative biology, Analytical Chemistry, 78(23):7918-7925.
Third Party Observation dated Jun. 14, 2018 in Japanese patent application No. 2016-537867.
Official Action dated Jul. 30, 2018 in Japanese patent application No. 2016-537867.
Advisory Action dated Dec. 2, 2019 in U.S. Appl. No. 15/055,407.
Advisory Action dated Nov. 29, 2019 in U.S. Appl. No. 15/084,307.
Alexandra M. Ewing of Richards, Layton and Finger, P.A., Entry of Appearance dated Jan. 18, 2019 in the USDC District of Delaware, C.A. No. 18-1800-RGA, 1 pp.
Cao et al., "Comprehensive single-cell transcriptional profiling of a multicellular organism," Science 2017, 357, 661-667.
Caruccio et al., "Nextera (TM) Technology for NGS DNA Library Preparation: Simultaneous Fragmentation and Tagging by in Vitro Transposition," EpiBio 2009, 16(3), 4-6.
Civil Cover Sheet filed Nov. 15, 2018 in the USDC for the District of Delaware, C.A. 18-1800-RGA, 1 pp.
Complaint filed in Becton, Dickinson and Company and Cellular Research Inc. v. 10X Genomics, Inc. dated Nov. 15, 2018 in the USDC for the District of Delaware, C.A. 18-1800-RGA, 141 pp.
Cotten et al., "Selection of proteins with desired properties from natural proteome libraries using mRNA display," Nature Protocols 2011, 6, 1163-1182.
Defendant 10X Genomic Inc.'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.
Defendant 10X Genomic's Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomic's Notice of Service for Initial Disclosures served to Opposing Counsel, dated Jun. 7, 2019 in the USDC for the District of Delaware, C.A. 18-1800-RGA, 2 pp.
Defendant 10X Genomic's Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.

(56) References Cited

OTHER PUBLICATIONS

Defendant 10X Genomics, Inc.'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s Rule 7.1 Disclosure Statement, dated Jan. 18, 2019 in the USDC District of Delaware, C.A. No. 18-1800-RGA, 1 pp. 1.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomics's Reply Brief in support of its Motion to Dismiss Pursuant to Federal Rule of Civil Procedure 12(b)(6), dated Apr. 12, 2019 in USDC District of Delaware, C.A. No. 18-1800 RGA, 15 pp.
Defendants 10X Genomics, Inc.'s Letter to Judge Andrews in Response to Plantiffs Letter of Supplemental Authority, dated Jul. 11, 2019 in the USDC for the District of Delaware, C.A. 18-1800-RGA, 2 pp.
Defendants 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.
Delley et al., "Combined aptamer and transcriptome sequencing of single cells," bioRxiv 2017, 1-10.
Evanko et al., "Hybridization chain reaction," Nature Methods 2004, 1(3), 186-187.
Examination Report dated Aug. 2, 2019 in European Patent Application No. 17202409.3.
Examination Report dated Dec. 12, 2018 in European Patent Application No. 16719706.0.
Examination Report dated Feb. 6, 2019 in European Patent Application No. 13754428.4.
Examination Report dated Jan. 2, 2019 in European Patent Application No. 16757986.1.
Examination Report dated Jul. 24, 2019 in European Patent Application No. 16714081.3.
Examination Report dated Jun. 18, 2019 in European Patent Application No. 16710551.9.
Examination Report dated Mar. 18, 2019 in Singapore Patent Application No. 11201405274W.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits 1-8 filed Feb. 8, 2019 in the USDC for the District of Delaware, C.A. 18-1800-RGA, 2997 pp.
Exhibits 1-8 filed Nov. 15, 2018 in the USDC for the District of Delaware, C.A. 18-1800-RGA, 2997 pp.
Exhibits 9-11 filed Feb. 8, 2019 in the USDC for the District of Delaware, C.A. 18-1800-RGA, 1182 pp.
Exhibits 9-11 filed Nov. 15, 2018 in the USDC for the District of Delaware, C.A. 18-1800-RGA, 1182 pp.
Exhibits A-D filed Jan. 18, 2019 in the USDC District of Delaware, C.A. No. 1:18-cv-01800-RGA, 47 pp.
Exhibits A-E, filed Mar. 1, 2019 in the USDC District of Delaware, C.A. No. 18-1800 RGA, 75 pp.
Extended European Search Report dated Mar. 22, 2019 in European Patent Application No. 18195513.9.
Final Office Action dated Apr. 22, 2019 in U.S. Appl. No. 16/219,553.
Final Office Action dated Dec. 4, 2019 in U.S. Appl. No. 15/596,364.
Final Office Action dated Mar. 1, 2019 in U.S. Appl. No. 16/012,584.
Final Office Action dated May 2, 2019 in U.S. Appl. No. 16/012,635.
Final Office Action dated May 3, 2019 in U.S. Appl. No. 15/937,713.
Final Office Action dated Oct. 2, 2019 in U.S. Appl. No. 15/084,307.
Final Office Action dated Sep. 18, 2019 in U.S. Appl. No. 15/055,407.
Flanigon et al., "Multiplex protein detection with DNA readout via mass spectrometry," N Biotechnol. 2013, 30(2), 153-158.
Fu et al., "Molecular indexing enables quantitative targeted RNA sequencing and reveals poor efficiencies in standard library preparation," PNAS 2014, 111(5), 1891-1896.
Gong et al., "Simple Method to Prepare Oligonucleotide-Conjugated Antibodies and Its Application in Multiplex Protein Detection in Single Cells," Bioconjugate Chem. 2016, 27, 217-225.
Han et al., "An approach to multiplexing an immunosorbent assay with antibody-oligonucleotide conjugates," Bioconjug Chem. 2010, 21(12), 2190-2196.
Holcomb et al., "Abstract 1853: Single-cell multiplexed profiling of protein-level changes induced by EGFR inhibitor gefitinib," Cancer Res 2016, 76(14 Suppl), Abstact 1853.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
International Preliminary Report on Patentability dated Mar. 26, 2019 in PCT Application No. PCT/US2017/053331.
International Preliminary Report on Patentability dated Aug. 15, 2019 in PCT Application No. PCT/US2018/014385.
International Search Report and Written Opinion dated Jun. 24, 2019 in PCT Application No. PCT/US2019/030175.
International Search Report and Written Opinion dated Nov. 27, 2019 in PCT Application No. PCT/US2019/046549.
International Search Report and Written Opinion dated Oct. 16, 2019 in PCT Application No. PCT/US2019/030245.
International Search Report and Written Opinion dated Oct. 8, 2019 in PCT Application No. PCT/US2019/043949.
Invitation to Pay Fees dated Nov. 26, 2019 in PCT Application No. PCT/US2019/048179.
Jason J. Rawnsley of Richards, Layton and Finger, P.A., Entry of Appearance dated Jan. 18, 2019 in the USDC District of Delaware, C.A. No. 18-1800-RGA, 1 pp.
Joint Stipulation and Order to Extend Time to Respond to Plantiff's First Amended Complaint, dated Feb. 21, 2019 in the USDC for the District of Delaware, C.A. 18-1800-RGA, 2 pp.
Joint Stipulation and Order to Extended Time to Submit Agreed Document Production Protocol, filed Jun. 28, 2019 in the USDC for the District of Delaware, C.A. 18-1800 (RGA), 1 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.
Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Request Extended Time to Submit Agreed Document Production Protocol, dated Jul. 11, 2019 in the USDC for the District of Delaware, C.A. 18-1800 (RGA), 1 pp.
Kang et al., "Application of multi-omics in single cells," Ann Biotechnol. 2018, 2(1007), 1-8.
Kausch et al., "Organelle isolation by magnetic immunoabsorption," Biotechniques 1999, 26(2), 336-343.
Kozlov et al., "A high-complexity, multiplexed solution-phase assay for profiling protease activity on microarrays," Comb Chem High Throughput Screen 2008, 11(1), 24-35.
Lass-Napiorkowska et al., "Detection methodology based on target molecule-induced sequence-specific binding to a single-stranded oligocleotide," Anal Chem. 2012, 84(7), 3382-3389.
Letter to Judge Andrews regarding Agreement on Proposed Scheduling Order, dated May 7, 2019 in the USDC for the District of Delaware, C.A. 18-1800-RGA, 1 pp.
Letter to Judge Andrews regarding Notice of Supplemental Authority, dated Jul. 10, 2019 in the USDC for the District of Delaware, C.A. 18-1800(RGA), 2pp.
Letter to Judge Richard G. Andrews Requesting a Rule 16 Conference, dated Apr. 15, 2019 in the USDC for the District of Delaware, C.A. 18-1800 (RGA), 1 pp.

(56) References Cited

OTHER PUBLICATIONS

Motion and Order for Admission Pro Hac Vice Pursuant to Local Rule 83.5, dated Jan. 24, 2019 in the USDC District of Delaware, C.A. No. 18-1800-RGA, 7 pp.
Non-Final Office Action dated Aug. 20, 2019 in U.S. Appl. No. 15/715,028.
Non-Final Office Action dated Feb. 19, 2019 in U.S. Appl. No. 14/381,526.
Non-Final Office Action dated Jul. 9, 2019 in U.S. Appl. No. 15/596,364.
Non-Final Office Action dated Jun. 17, 2019 in U.S. Appl. No. 14/381,488.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Nov. 29, 2019 in U.S. Appl. No. 15/937,713.
Non-Final Office Action dated Sep. 18, 2019 in U.S. Appl. No. 16/194,819.
Notice of Allowance dated Jan. 9, 2019 in U.S. Appl. No. 15/603,239.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Nov. 29, 2019 in U.S. Appl. No. 16/012,635.
Notice of Allowance dated Sep. 24, 2019 in U.S. Appl. No. 15/217,886.
Notice of Reason for Refusal dated Nov. 21, 2019 in Korean Patent Application No. 10-20167008144.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.
Notice, Consent, and Reference of a Civil Action to a Magistrate Judge (Rule 73.1), filed Nov. 15, 2018 in the USDC for the District of Delaware, C.A. 18-1800-RGA, 3 pp.
Office Action dated Dec. 13, 2018 in Canadian Patent Application No. 2865575.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Scheduling ADR Mediation Teleconference, filed May 13, 2019 in the USDC for the District of Delaware, C.A. 18-1800-RGA, 4pp.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Purusant to Rule 26(c) of the Federal Rules of Civil Procedure, filed Jun. 20, 2019 in the USDC for the District of Delaware, C.A. 18-1800 (RGA), 26 pp.
Rule 7.1 Disclosure Statement dated Nov. 15, 2018 in the USDC for the District of Delaware, C.A. 18-1800-RGA, 1 pp.
Report on the Filing or Determination of an Action Regarding a Patent or Trademark filed Nov. 15, 2018 in the USDC for the District of Delaware, C.A. 18-1800-RGA, 2 pp.
Restriction Requirement dated Jun. 19, 2019 in U.S. Appl. No. 15/596,364.
Restriction Requirement dated Mar. 29, 2019 in U.S. Appl. No. 15/715,028.
Restriction Requirement dated Sep. 20, 2019 in U.S. Appl. No. 15/875,816.
Scheduling conference pursuant to Local Rule 16.1(b), filed May 7, 2019 in the USDC for the District of Delaware, C.A. 18-1800-RGA, 10 pp.
Scheduling Order Signed by Judge Andrews, dated May 8, 2019 in the USDC for the District of Delaware, C.A. 18-1800-RGA, 10 pp.
Sogin et al., "Microbial diversity in the deep sea and the underexplored "rare biosphere"," PNAS 2008, 103(32), 12115-12120.
Statement of Opposition filed against European Patent No. EP2414548B1 on Jul. 26, 2016.
Stipulated Protective Order Purusant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Summons in a Civil Action to Defendant 10X Genomics, Inc. filed Nov. 16, 2018 in the USDC for the District of Delaware, Civil Action No. 18-1800, 2 pp.
Sun et al.,"Ultra-deep profiling of alternatively spliced *Drosophila* Dscam isoforms by circularization-assisted multi-segment sequencing," EMBO J. 2013, 32(14), 2029-2038.
Unopposed Motion to Extend Time for Defendant's Response, dated Dec. 4, 2018 in the USDC for the District of Delaware, C.A. 18-1800-(RGA), 2 pp.
Wang et al.,"Combining Gold Nanoparticles with Real-Time Immuno-PCR for Analysis of HIV p24 Antigens," Proceedings of ICBBE 2007, 1198-1201.
Weibrecht et al., "Proximity ligation assays: a recent addition to the proteomics toolbox," Expert Rev. Proteomics 2010, 7(3), 401-409.
Zagordi et al., "Error correction of next-generation sequencing data and reliable estimation of HIV quasispecies," Nucleic Acids Research 2010, 38(21), 7400-7409.
Zhou et al., "Photocleavable Peptide-Oligonucleotide Conjugates for Protein Kinase Assays by MALDI-TOF MS," Mol. BioSyst. 2012, 8, 2395-2404.
Zhu et al., "Reverse Transcriptase Template Switching: a Smart Approach for Full-Length cDNA Library Construction," BioTechniques 2001, 30(4), 892-897.
10X Genomics Inc's, Notice of Service of Technical Documents, dated Jul. 8, 2019 in the USDC for the District of Delaware, C.A. 18-1800-RGA, 2 pp.
10X Genomic's Request for Oral Argument Under D. Del. LR 7.1.4, dated Apr. 18, 2019 in the USDC for the District of Delaware, C.A. 18-1800-RGA 2 pp.

\* cited by examiner

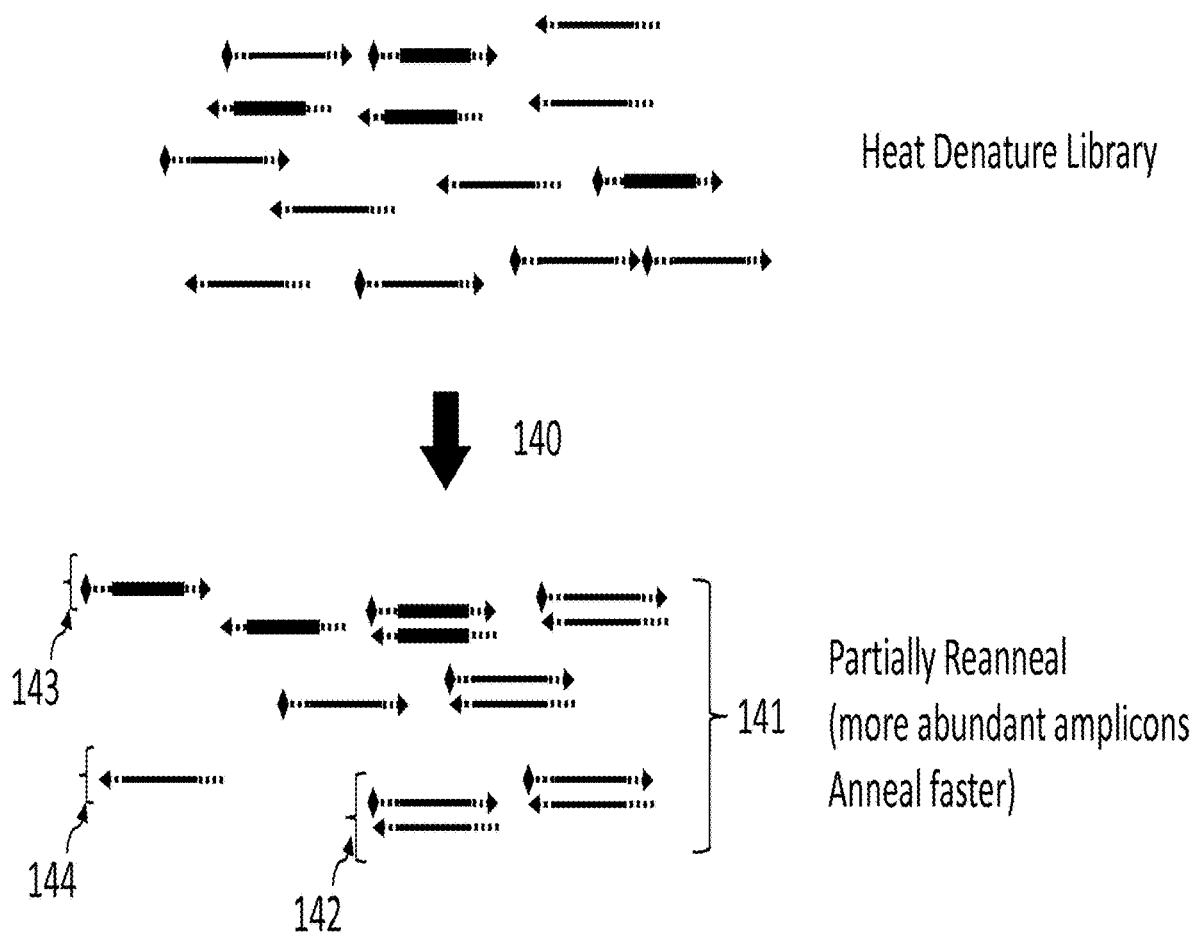
FIG. 1, continued

*FIG. 1, continued*
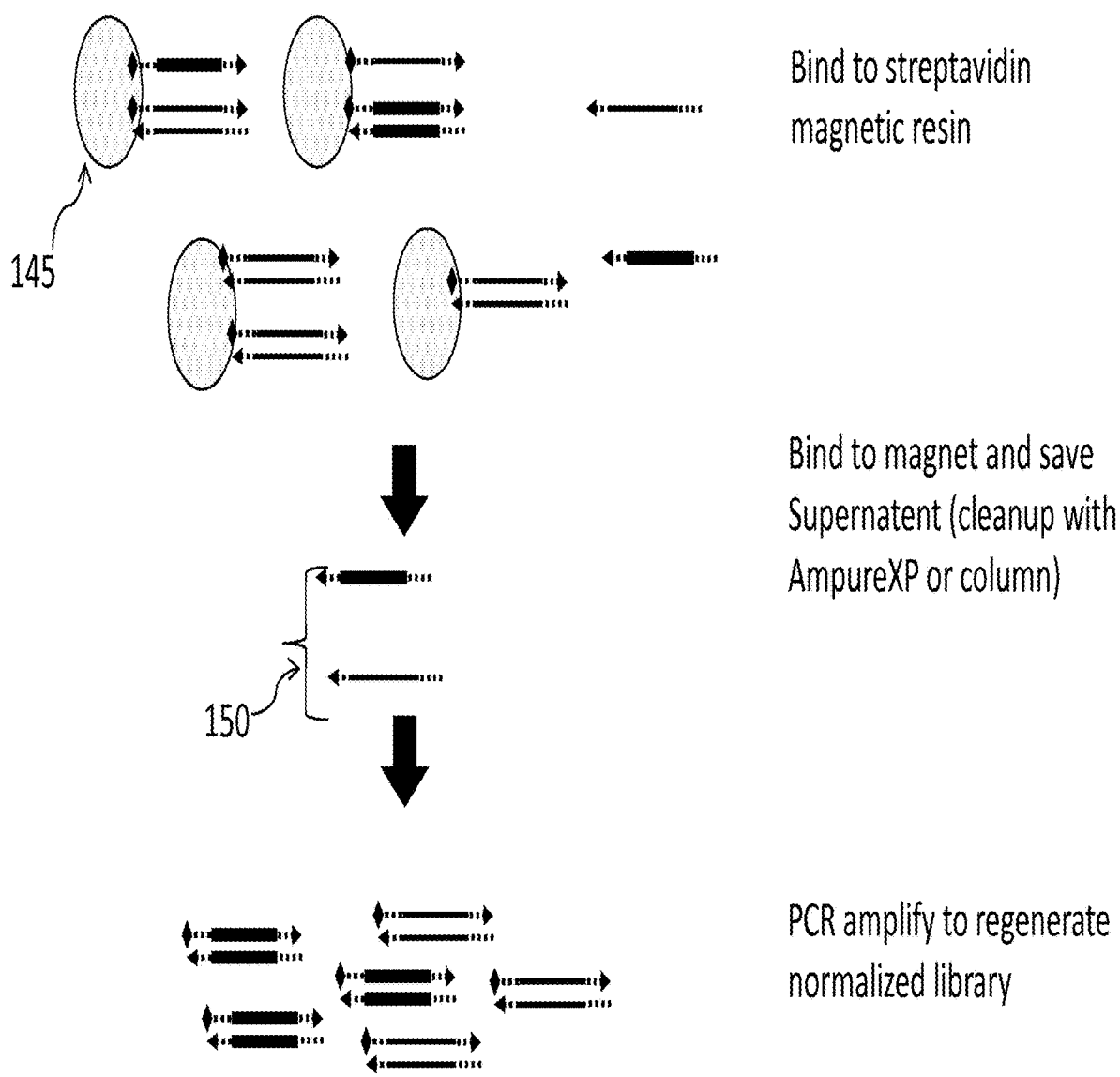

METHODS AND COMPOSITIONS FOR LIBRARY NORMALIZATION

RELATED APPLICATIONS

This application is based upon and claims the benefit under 35 U.S.C. § 119(e) of U.S. Provisional Patent Application Ser. No. 62/217,220, filed Sep. 11, 2015. The content of the related application is incorporated herein by reference in its entirety for all purposes.

BACKGROUND

In many applications, particularly sequencing and library screening, researchers want to assess the entire catalogue of nucleic acids in a sample or library. However, the nucleic acids in a sample (e.g. a cDNA library) are often in a broad range of concentrations ranging several orders a magnitude. This greatly increases the amount of sequencing or screening necessary to fully assess sample. To overcome this, researchers often want to work with a normalized library where the concentrations of different nucleic acids are all at a similar concentration, so that less redundant effort is required to interrogate new molecules.

SUMMARY

Some embodiments disclosed herein provide methods of removing high abundance species from a plurality of nucleic acid molecules, comprising: hybridizing a plurality of first oligonucleotides comprising a binding moiety with a first plurality of nucleic acid molecules, wherein the first plurality of nucleic acid molecules comprises at least one high abundance species; extending the plurality of first oligonucleotides to generate a plurality of complementary strands of the first plurality of nucleic acid molecules comprising the binding moiety; denaturing a plurality of double-stranded nucleic acid molecules comprising the plurality of complementary strands of the first plurality of nucleic acid molecules; partially reannealing the plurality of complementary strands of the first plurality of nucleic acid molecules; and removing the reannealed complementary strands of the first plurality of nucleic acid molecules by a capture molecule immobilized on one or more solid support to generate a second plurality of nucleic acid molecules, wherein the capture molecules specifically bind to the binding moiety, whereby the content of the at least one high abundance species in the second plurality of nucleic acid molecules is reduced in comparison to the content of the at least one high abundance species in the first plurality of nucleic acid molecules.

In some embodiments, the binding moiety is a functional group selected from the group consisting of biotin, streptavidin, heparin, an aptamer, a click-chemistry moiety, digoxigenin, primary amine(s), carboxyl(s), hydroxyl(s), aldehyde(s), ketone(s), and any combination thereof. In some embodiments, the binding moiety is biotin. In some embodiments, the capture molecule is streptavidin. In some embodiments, the methods further comprise synthesizing a second strand for at least one of the plurality of complementary strands of the first plurality of nucleic acid molecules to generate one or more of the plurality of double-stranded nucleic acid molecules comprising the plurality of complementary strands of the first plurality of nucleic acid molecules. In some embodiments, the synthesizing comprises hybridizing a plurality of second oligonucleotides to the plurality of complementary strands of the first plurality of nucleic acid molecules and extending the plurality of second oligonucleotide. In some embodiments, the plurality of first oligonucleotides or the plurality of second oligonucleotides comprises a universal primer binding site. In some embodiments, the methods further comprise amplifying the plurality of double-stranded nucleic acid molecules. In some embodiments, the first plurality of nucleic acid molecules comprises a plurality of high abundance species. In some embodiments, the at least one high abundance species represents at least 50% of the first plurality of nucleic acid molecules. In some embodiments, the at least one high abundance species represents at least 60% of the first plurality of nucleic acid molecules. In some embodiments, the at least one high abundance species represents at least 70% of the first plurality of nucleic acid molecules. In some embodiments, the reduction of the content of the at least one high abundance species is at least 80%. In some embodiments, the reduction of the content of the at least one high abundance species is at least 90%. In some embodiments, the reduction of the content of the at least one high abundance species is at least 95%. In some embodiments, the reduction of the content of the at least one high abundance species is at least 99%. In some embodiments, the second plurality of nucleic acid molecules comprises the plurality of high abundance species. In some embodiments, the plurality of high abundance species in the second plurality of nucleic acid molecules represents less than 50% of the second plurality of nucleic acid molecules. In some embodiments, the plurality of high abundance species in the second plurality of nucleic acid molecules represents less than 40% of the second plurality of nucleic acid molecules. In some embodiments, the plurality of high abundance species in the second plurality of nucleic acid molecules represents less than 30% of the second plurality of nucleic acid molecules. In some embodiments, first plurality of nucleic acid molecules comprises a plurality of low abundance species. In some embodiments, the plurality of low abundance species represents less than 10% of the first plurality of nucleic acid molecules. In some embodiments, the plurality of low abundance species represents less than 5% of the first plurality of nucleic acid molecules. In some embodiments, the plurality of low abundance species represents less than 1% of the first plurality of nucleic acid molecules. In some embodiments, the second plurality of nucleic acid molecules comprises the plurality of low abundance species. In some embodiments, the plurality of low abundance species in the second plurality of nucleic acid molecules represents at least 5% of the second plurality of nucleic acid molecules. In some embodiments, the plurality of low abundance species in the second plurality of nucleic acid molecules represents at least 10% of the second plurality of nucleic acid molecules. In some embodiments, the plurality of low abundance species in the second plurality of nucleic acid molecules represents at least 20% of the second plurality of nucleic acid molecules. In some embodiments, each of the first plurality of nucleic acid molecules or each of the second plurality of nucleic acid molecules comprises a stochastic barcode. In some embodiments, the methods further comprise sequencing the second plurality of nucleic acid molecules to generate a plurality of sequencing reads. In some embodiments, the sequencing reads for the plurality of high abundance species is less than 50% of the total sequencing reads. In some embodiments, the sequencing reads for the plurality of high abundance species is less than 40% of the total sequencing reads. In some embodiments, the sequencing reads for the plurality of high abundance species is less than 30% of the total sequencing reads. In some embodiments, the sequencing reads for the plurality of low abundance species is at least 5% of the total sequencing reads. In some embodiments, the sequencing reads for the plurality of low abundance species is at least 10% of the total sequencing reads. In some embodiments, the sequencing reads for the plurality of low abundance species is at least 20% of the total sequencing reads. In some embodiments, the methods further comprise adding a plurality of blockers during the partially reannealing step. In some embodiments, the plurality of blockers hybrids to the universal primer binding site of the first oligonucleotide or the universal primer binding site of the second oligonucleotide. In some embodiments, the plurality of blockers prevents hybridization between the universal primer binding site of the first oligonucleotide or the universal primer binding site of the second oligonucleotide and its complementary sequence.

Some embodiments disclosed herein provide methods of generating a normalized nucleic acid library, comprising: hybridizing a plurality of first oligonucleotides comprising a binding moiety with a plurality of nucleic acid targets; extending the plurality of first oligonucleotides to generate a plurality of complementary strands of the plurality of nucleic acid targets comprising the binding moiety; denaturing a plurality of double-stranded nucleic acid molecules comprising the plurality of complementary strands of the plurality of nucleic acid targets; partially reannealing the plurality of complementary strands of the plurality of nucleic acid targets; and removing the reannealed complementary strands of the plurality of nucleic acid targets by a capture molecule immobilized on one or more solid support, wherein the capture molecules specifically bind to the binding moiety, whereby a normalized nucleic acid library of the plurality of nucleic acid targets is generated.

In some embodiments, the binding moiety is a functional group selected from the group consisting of biotin, streptavidin, heparin, an aptamer, a click-chemistry moiety, digoxigenin, primary amine(s), carboxyl(s), hydroxyl(s), aldehyde(s), ketone(s), and any combination thereof. In some embodiments, the binding moiety is biotin. In some embodiments, the capture molecule is streptavidin. In some embodiments, the methods further comprise synthesizing a second strand for one or more of the plurality of complementary strands of the plurality of nucleic acid targets to generate one or more of the plurality of double-stranded nucleic acid molecules comprising the plurality of complementary strands of the plurality of nucleic acid targets. In some embodiments, the synthesizing comprises hybridizing a plurality of second oligonucleotides to the plurality of complementary strands of the plurality of nucleic acid targets and extending the plurality of second oligonucleotide. In some embodiments, the plurality of first oligonucleotides or the plurality of second oligonucleotides comprises a universal primer binding site. In some embodiments, the methods further comprise amplifying the plurality of double-stranded nucleic acid molecules. In some embodiments, the plurality of nucleic acid targets comprises a plurality of low abundance nucleic acid targets. In some embodiments, the plurality of low abundance nucleic acid targets represents less than 10% of the plurality of nucleic acid targets. In some embodiments, the plurality of low abundance nucleic acid targets represents less than 5% of the plurality of nucleic acid targets. In some embodiments, the plurality of low abundance nucleic acid targets represents less than 1% of the plurality of nucleic acid targets. In some embodiments, the normalized nucleic acid library of the plurality of nucleic acid targets comprises the plurality of low abundance nucleic acid targets. In some embodiments, the plurality of low abundance nucleic acid targets in the normalized nucleic acid library represents at least 5% of the plurality of nucleic acid targets in the normalized nucleic acid library. In some embodiments, the plurality of low abundance nucleic acid targets in the normalized nucleic acid library represents at least 10% of the plurality of nucleic acid targets in the normalized nucleic acid library. In some embodiments, the plurality of low abundance nucleic acid targets in the normalized nucleic acid library represents at least 20% of the plurality of nucleic acid targets in the normalized nucleic acid library. In some embodiments, the plurality of nucleic acid targets comprises a plurality of high abundance nucleic acid targets. In some embodiments, the plurality of high abundance nucleic acid targets represents at least 50% of the plurality of nucleic acid targets. In some embodiments, the plurality of high abundance nucleic acid targets represents at least 60% of the plurality of nucleic acid targets. In some embodiments, the plurality of high abundance nucleic acid targets represents at least 70% of the plurality of nucleic acid targets. In some embodiments, the content of the plurality of high abundance species in the normalized nucleic acid library is reduced by at least 80%. In some embodiments, the content of the plurality of high abundance species in the normalized nucleic acid library is reduced by at least 90%. In some embodiments, the content of the plurality of high abundance species in the normalized nucleic acid library is reduced by at least 95%. In some embodiments, the content of the plurality of high abundance species in the normalized nucleic acid library is reduced by at least 99%. In some embodiments, the normalized nucleic acid library of the plurality of nucleic acid targets comprises the plurality of high abundance nucleic acid targets. In some embodiments, the plurality of high abundance nucleic acid targets in the normalized nucleic acid library represents less than 50% of the plurality of nucleic acid targets in the normalized nucleic acid library. In some embodiments, the plurality of high abundance nucleic acid targets in the normalized nucleic acid library represents less than 40% of the plurality of nucleic acid targets in the normalized nucleic acid library. In some embodiments, the plurality of high abundance nucleic acid targets in the normalized nucleic acid library represents less than 30% of the plurality of nucleic acid targets in the normalized nucleic acid library. In some embodiments, each of the plurality of first oligonucleotides or each of the plurality of second oligonucleotides comprises a stochastic barcode. In some embodiments, the methods further comprise sequencing the normalized nucleic acid library to generate a plurality of sequencing reads. In some embodiments, the sequencing reads for the plurality of high abundance nucleic acid targets is less than 50% of the total sequencing reads. In some embodiments, the sequencing reads for the plurality of high abundance nucleic acid targets is less than 40% of the total sequencing reads. In some embodiments, the sequencing reads for the plurality of high abundance nucleic acid targets is less than 30% of the total sequencing reads. In some embodiments, the sequencing reads for the plurality of low abundance nucleic acid targets is at least 5% of the total sequencing reads. In some embodiments, the sequencing reads for the plurality of low abundance nucleic acid targets is at least 10% of the total sequencing reads. In some embodiments, the sequencing reads for the plurality of low abundance nucleic acid targets is at least 20% of the total sequencing reads. In some embodiments, the methods further comprise adding a plurality of blockers during the partially reannealing step. In some embodiments, the plurality of blockers hybrids to the universal primer binding site of the first oligonucleotide or the universal primer binding site of the second oligonucleotide. In some embodiments, the plurality of blockers prevents hybridization between the universal primer binding site of the first oligonucleotide or the universal primer binding site of the second oligonucleotide and its complementary sequence. In some embodiments, the plurality of nucleic acid targets comprises mRNA. In some embodiments, the plurality of nucleic acid targets comprises mitochondrial mRNA. In some embodiments, the plurality of nucleic acid targets comprises ribosomal protein mRNA. In some embodiments, the low abundance nucleic acid targets comprise 7,000 genes with the lowest number of transcripts. In some embodiments, the low abundance nucleic acid targets comprise 4,000 genes with the lowest number of transcripts. In some embodiments, the low abundance nucleic acid targets comprise 2,000 genes with the lowest number of transcripts. In some embodiments, the plurality of first oligonucleotides comprises target-specific primers. In some embodiments, the plurality of first oligonucleotides comprises non-target-specific primers. In some embodiments, the plurality of nucleic acid targets comprises cDNA. In some embodiments, the plurality of nucleic acid targets comprises genomic DNA. In some embodiments, the high abundance nucleic acid targets comprise short tandem repeat sequences. In some embodiments, the high abundance nucleic acid targets comprise telomeric sequences. In some embodiments, the high abundance nucleic acid targets comprise centromeric sequences. In some embodiments, the plurality of nucleic acid targets is from a single cell.

Some embodiments disclosed herein provide methods of generating a normalized nucleic acid library, comprising: hybridizing a plurality of first oligonucleotides comprising a binding moiety with a plurality of nucleic acid targets in an unnormalized nucleic acid library; extending the plurality of first oligonucleotides to generate a plurality of complementary strands of the plurality of nucleic acid targets comprising the binding moiety; denaturing a plurality of double-stranded nucleic acid molecules comprising the plurality of complementary strands of the plurality of nucleic acid targets; partially reannealing the plurality of complementary strands of the plurality of nucleic acid targets; and removing the reannealed complementary strands of the plurality of nucleic acid targets, whereby a normalized nucleic acid library of the plurality of nucleic acid targets is generated.

In some embodiments, the unnormalized nucleic acid library comprises one or more high abundance nucleic acid targets and one or more low abundance nucleic acid targets. In some embodiments, the one or more high abundance nucleic acid targets represents at least 50% of the unnormalized nucleic acid library. In some embodiments, the one or more high abundance nucleic acid targets represents at least 60% of the unnormalized nucleic acid library. In some embodiments, the one or more high abundance nucleic acid targets represents at least 70% of the unnormalized nucleic acid library. In some embodiments, the content of the one or more high abundance nucleic acid targets in the normalized nucleic acid library is reduced by at least 80%. In some embodiments, the content of the one or more high abundance nucleic acid targets in the normalized nucleic acid library is reduced by at least 90%. In some embodiments, the content of the one or more high abundance nucleic acid targets in the normalized nucleic acid library is reduced by at least 95%. In some embodiments, the content of the one or more high abundance nucleic acid targets in the normalized nucleic acid library is reduced by at least 99%. In some embodiments, the one or more low abundance nucleic acid targets represents less than 10% of the unnormalized nucleic acid library. In some embodiments, the one or more low abundance nucleic acid targets represents less than 5% of the unnormalized nucleic acid library. In some embodiments, the one or more low abundance nucleic acid targets represents less than 1% of the unnormalized nucleic acid library. In some embodiments, the one or more low abundance nucleic acid targets represents at least 5% of the normalized nucleic acid library. In some embodiments, the one or more low abundance nucleic acid targets represents at least 10% of the normalized nucleic acid library. In some embodiments, the one or more low abundance nucleic acid targets represents at least 20% of the normalized nucleic acid library. In some embodiments, the one or more high abundance nucleic acid targets represents less than 50% of the normalized nucleic acid library. In some embodiments, the one or more high abundance nucleic acid targets represents less than 40% of the normalized nucleic acid library. In some embodiments, the one or more high abundance nucleic acid targets represents less than 30% of the normalized nucleic acid library. In some embodiments, the unnormalized nucleic acid library is a cDNA library. In some embodiments, the unnormalized nucleic acid library is a genomic library. In some embodiments, the unnormalized nucleic acid library is a single-cell nucleic acid library.

In one aspect, the disclosure provides for a method of nucleic acid library normalization comprising: generating an asymmetrically labelled double-stranded cDNA library, wherein one strand of double-stranded cDNAs of the cDNA library comprise a binding moiety; denaturing and partially re-annealing strands of the double-stranded cDNAs in the library, thereby generating a mixture of re-annealed cDNAs molecules comprising the binding moiety, single-stranded molecules comprising the binding moiety, and single-stranded molecules lacking the binding moiety; and removing the molecules comprising the binding moiety, while leaving behind the single-stranded molecules lacking the binding moiety, thereby producing a normalized library. In some embodiments, the generating comprises reverse transcribing an mRNA into a first cDNA strand using a primer comprising the binding moiety. In some embodiments, the primer comprises a stochastic barcode. In some embodiments, the method further comprises generating a second cDNA strand complementary to the first cDNA strand, thereby generating the double-stranded cDNA. In some embodiments, the generating comprises performing primer extension on a DNA molecule using a primer comprising the binding moiety, thereby generating the double-stranded cDNA. In some embodiments, the binding moiety is selected from the group consisting of: biotin and streptavidin. In some embodiments, the binding moiety is attached to the sense strand of the double-stranded cDNA. In some embodiments, the binding moiety is attached to the anti-sense strand of the double-stranded cDNA. In some embodiments, the denaturing comprises heating the double-stranded cDNAs. In some embodiments, the denaturing comprises denaturing at least 50% of the double-stranded cDNAs. In some embodiments, the denaturing comprises denaturing at least 90% of the double-stranded cDNAs. In some embodiments, the re-annealed cDNAs are from a highly abundant nucleic acid species. In some embodiments, strands of the re-annealed cDNAs re-anneal at least twice as fast a strands of the double-stranded cDNA library from a less abundant nucleic acid species. In some embodiments, strands of the re-annealed cDNAs re-anneal at least five times as fast a strands of the double-stranded cDNA library from a less abundant nucleic acid species. In some embodiments, strands of the re-annealed cDNAs re-anneal at a higher abundance than strands of the double-stranded cDNA library from a less abundant nucleic acid species. In some embodiments, the removing comprises contacting the molecules with a solid support. In some embodiments, the solid support comprises a capture moiety that binds to the binding moiety. In some embodiments, the capture moiety is selected from the group consisting of: biotin and streptavidin. In some embodiments, the solid support is a bead. In some embodiments, the solid support is magnetic. In some embodiments, the re-annealed cDNAs are double-stranded. In some embodiments, the single-stranded molecules lacking the binding moiety are the complement of single strands removed during the removing. In some embodiments, the method further comprises amplifying the normalized library. In some embodiments, the amplifying comprises generating a double-stranded nucleic acid from single stranded nucleic acids in the normalized library. In some embodiments, the method further comprises adding adaptors to the double-stranded nucleic acid. In some embodiments, the adding adaptors comprises ligating the adaptors to the double-stranded nucleic acid. In some embodiments, the adding adaptors comprises introducing the adaptors to the double-stranded nucleic acid through amplification. In some embodiments, the adaptors comprise sequencing flow cell sequences. In some embodiments, the method further comprises sequencing the double-stranded nucleic acids. In some embodiments, a most abundant species in the normalized library is at most 20 times more abundant than a least abundant species in the normalized library. In some embodiments, a most abundant species in the normalized library is at most 10 times more abundant than a least abundant species in the normalized library. In some embodiments, a most abundant species in the normalized library is at most 5 times more abundant than a least abundant species in the normalized library.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
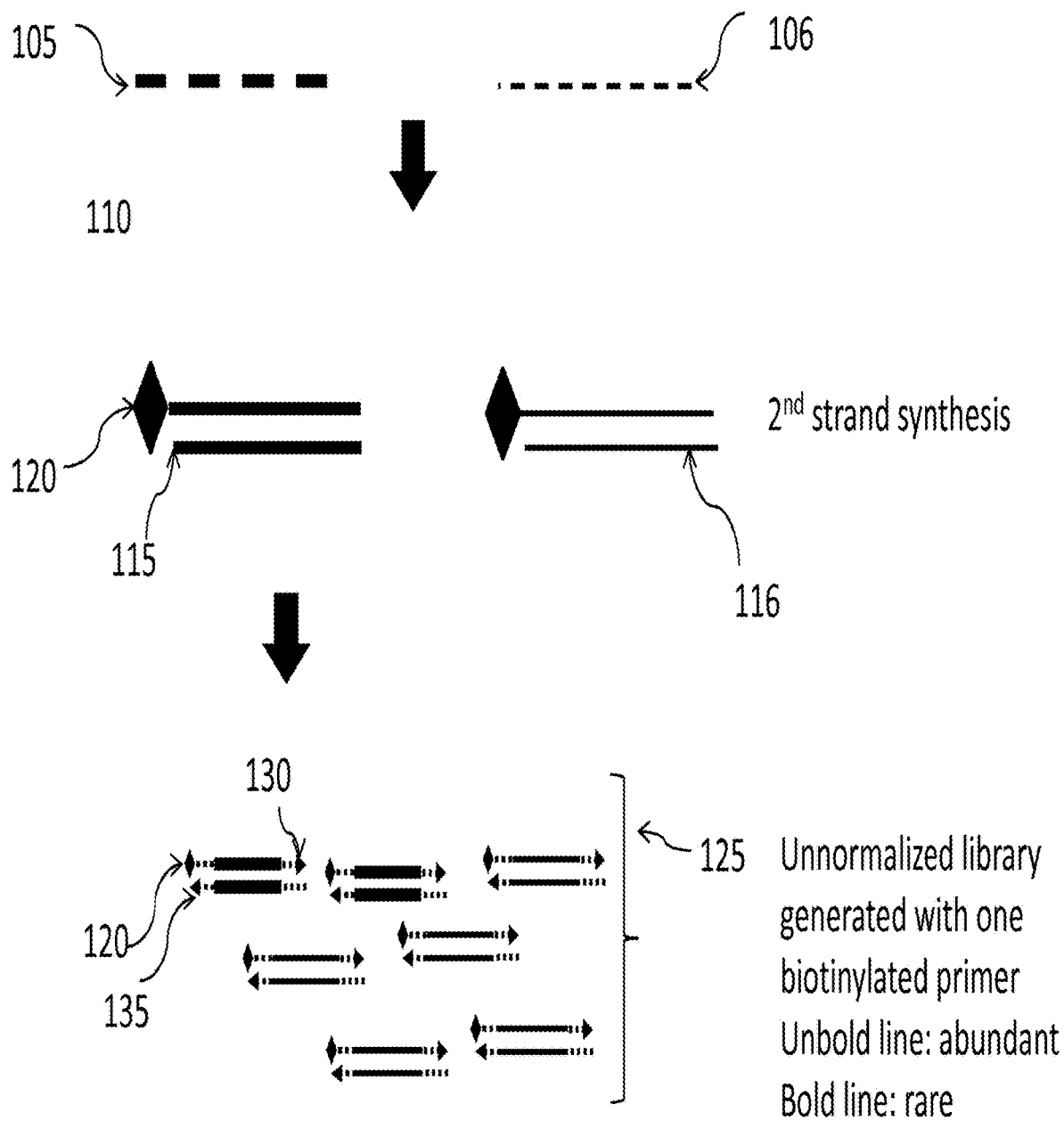
FIG. 1 illustrates an exemplary embodiment of the library normalization method of the disclosure.

All publications, patents, and patent applications mentioned in this specification are herein incorporated by reference for all purposes to the same extent as if each individual publication, patent, or patent application was specifically and individually indicated to be incorporated by reference.

Most library normalization strategies are based on one of two principles. The first is hybridizing the library to another set of nucleic acids where the sequences are uniformly represented, such as the genomic DNA from the source organism, and retaining the hybridized fraction. The other approach relies on the concentration dependence of solution hybridization. When a set of dsDNA molecules are denatured, they will rehybridize at a rate proportional to the square of their original concentrations. The methods, compositions and kits disclosed herein, in some embodiments, exploit this property for library normalization by denaturing a mixture and only allowing it to partially reanneal; proportionally, much more of the high concentration species will have rehybridized to dsDNA while less abundant species will still be predominantly single stranded.

The methods, compositions and kits disclosed herein, in some embodiments, can avoid the use of physical and enzymatic separation of ssDNA and dsDNA fractions during library normalization. During initial library preparation, the library is asymmetrically labeled on one end with a binding moiety (for example by PCR with one 5' biotinylated primer and another unlabeled primer). After denaturation and partial reannealing, all of the labeled strands are captured on a support matrix, such as paramagnetic streptavidin beads, and the bound and unbound fractions are separated. Highly abundant sequences will be predominantly rehybridized, and both strands will be removed in the bound fraction. However, low abundance sequences will be less likely to rehybridize, so the complement of the labeled strand will be present in the unbound fraction. The unbound fraction would represent a normalized library, and could either be used directly or further amplified for downstream applications.

Definitions

Unless otherwise defined, all technical terms used herein have the same meaning as commonly understood by one of ordinary skill in the art in the field to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "attached", or "immobilized" to one another or to a common solid or semisolid surface. An association may refer to covalent or non-covalent means for attaching labels to solid or semi-solid supports such as beads. An association may comprise hybridization between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

As used herein, a "nucleic acid" can generally refer to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backgone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or flurescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone of the nucleic acid can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (Hpyrido(3',':4,5)pyrrolo[2,3-d] pyrimidin-2-one).

As used herein, the term "quasi-symmetric stochastically barcoded nucleic acid" can refer to a molecule comprising a stochastic barcode of the disclosure and ends that are symmetric enough to hybridize together to form a panhandle structure (e.g., for suppression PCR), but may not be identical. A quasi-symmetric stochastically barcoded nucleic acid can behave like a symmetric nucleic acid, but have an asymmetric sequence.

As used herein, the term "sample" can refer to a composition comprising targets. Suitable samples for analysis by the disclosed methods, devices, and systems include cells, single cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be used interchangeably with the term "bead." As used herein, "solid support" and "substrate" can be used interchangeably.

As used herein, the term "stochastic barcode" can refer to a polynucleotide sequence comprising labels of the disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids. As used herein, "target" can be used interchangeably with "species".

The term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

Methods of Removing High Abundance Species

Some embodiments disclosed herein provide methods of removing high abundance species from a plurality of nucleic acid molecules. In some embodiment, the methods disclosed herein can reduce the content of high abundance species from a plurality of nucleic acid molecules without significantly removing the low abundance species or the intermediate abundance species from the plurality of nucleic acid molecules. As used herein, "significantly removing" refers to removing at least 10%, at least 20%, at least 30%, at least 40%, at least 50% or more of a low abundance species or intermediate abundance species from the plurality of nucleic acid molecules. In some embodiments, the methods disclosed herein can remove high abundance species and the intermediate abundance species from a plurality of nucleic acid molecules without significantly removing the low abundance species from the plurality of nucleic acid molecules.

As used herein, a "species" refers to the polynucleotides (for example, single-stranded polynucleotides) in the plurality of nucleic acid molecules that are the same or the complement of one another, or are capable of hybridize to one another, or are transcripts from the same genetic locus, or encode the same protein or fragment thereof, etc. In some embodiments, members of a species are at least 80%, at least 90%, at least 95%, at least 98%, at least 99%, or 100% homologous to one another, or complement thereof. In some embodiments, members of a species can hybridize to one another under high stringent hybridization conditions. In some embodiments, members of a species can hybridize to one another under moderate stringent hybridization conditions. In some embodiments, members of a species can hybridize to one another under low stringent hybridization conditions. In some embodiments, members of a species are transcripts from the same genetic locus and the transcripts can be of the same or different length. The species is, in some embodiments, cDNA or mRNA.

As used herein, a "high abundance species" refers to a species that is present in high amount in the plurality of nucleic acids, for example the species can represent at least 1%, 2%, 3%, 4%, 5%, 6%, 7%, 8%, 9%, 10%, 20%, 30%, 40%, 50%, or more of the plurality of nucleic acid molecules. In some embodiments, the plurality of nucleic acid molecules can comprise at least 1, at least 2, at least 3, at least 4, at least 5, at least 10, at least 20, at least 50, at least 100, at least 200, at least 500, at least 1,000, or more, high abundance species. In some embodiments, the total of all the high abundance species represent at least 10%, at least 20%, at least 30%, at least 40%, at least 50%, at least 60%, at least 70%, at least 80%, or more of the plurality of nucleic acid molecules. In some embodiments, high abundance species can comprise polynucleotides encoding one or more ribosomal proteins. In some embodiments, high abundance species can comprise polynucleotides encoding one or more mitochondrial proteins. In some embodiments, high abundance species can comprise polynucleotides encoding one or more housekeeping proteins.

As used herein, an "intermediate abundance species" refers to a species that is present in an amount in the plurality of nucleic acid that is lower than at least one species in the plurality of nucleic acid and is higher than at least one other species in the plurality of nucleic acid. In some embodiments, an intermediate abundance species can represent about 10%, 5%, 4%, 3%, 2%, 1%, 0.1%, 0.01%, or a range between any two of the above values, of the plurality of nucleic acid molecules. In some embodiments, the plurality of nucleic acid molecules can comprise at least 1, at least 2, at least 3, at least 4, at least 5, at least 10, at least 20, at least 50, at least 100, at least 200, at least 500, at least 1,000, or more, intermediate abundance species. In some embodiments, the total of all the intermediate abundance species represent about 1%, about 2%, about 3%, about 4%, about 5%, about 10%, about 20%, about 30%, or a range between any two of the above values, of the plurality of nucleic acid molecules.

As used herein, a "low abundance species" refers to a species that is present in low amount in the plurality of nucleic acids, for example the species can represent less than 1%, 0.1%, 0.01%, 0.001%, 0.0001%, or less of the plurality of nucleic acid molecules. In some embodiments, the plurality of nucleic acid molecules can comprise at least 1, at least 2, at least 3, at least 4, at least 5, at least 10, at least 20, at least 50, at least 100, at least 200, at least 500, at least 1,000, or more, low abundance species. In some embodiments, the total of all the low abundance species represent less than 20%, less than 10%, less than 5%, less than 4%, less than 3%, less than 2%, less than 1%, less than 0.1%, or less of the plurality of nucleic acid molecules. In some embodiments, low abundance species can comprise polynucleotides encoding one or more transcription factors. In some embodiments, high abundance species can comprise polynucleotides encoding one or more T cell receptors. In some embodiments, high abundance species can comprise polynucleotides encoding one or more antibodies.

In some embodiments, the methods and compositions disclosed herein can reduce the content of one or more high abundance species from the plurality of nucleic acid molecules. For example, the methods and compositions disclosed herein can reduce the content of at least 1, at least 2, at least 3, at least 4, at least 5, at least 10, at least 20, at least 50, at least 100, at least 200, at least 500, at least 1,000, or more, high abundance species. In some embodiments, the methods and compositions disclosed herein can reduce the content by at least 10%, at least 20%, at least 30%, at least 40%, at least 50%, at least 60%, at least 70%, at least 80%, at least 90%, at least 95%, or 100% of each of the one or more high abundance species from the plurality of nucleic acid molecules. In some embodiments, the methods and compositions disclosed herein can reduce the content by at least 10%, at least 20%, at least 30%, at least 40%, at least 50%, at least 60%, at least 70%, at least 80%, at least 90%, at least 95%, or 100% of at least one of the one or more high abundance species from the plurality of nucleic acid molecules. In some embodiments, the methods and compositions disclosed herein can reduce the content by at least 10%, at least 20%, at least 30%, at least 40%, at least 50%, at least 60%, at least 70%, at least 80%, at least 90%, at least 95%, or 100% of the total of high abundance species from the plurality of nucleic acid molecules.

In some embodiments, the methods and compositions disclosed herein can reduce the content of one or more high abundance species from the plurality of nucleic acid molecules without significantly removing the low abundance species or the intermediate abundance species from the plurality of nucleic acid molecules. In some embodiments, the methods and compositions disclosed herein can reduce the content by at least 10%, at least 20%, at least 30%, at least 40%, at least 50%, at least 60%, at least 70%, at least 80%, at least 90%, at least 95%, or 100% of each of the one or more high abundance species from the plurality of nucleic acid molecules without significantly removing the low abundance species or the intermediate abundance species from the plurality of nucleic acid molecules. In some embodiments, the methods and compositions disclosed herein can reduce the content by at least 10%, at least 20%, at least 30%, at least 40%, at least 50%, at least 60%, at least 70%, at least 80%, at least 90%, at least 95%, or 100% of the total of high abundance species from the plurality of nucleic acid molecules without significantly removing the low abundance species or the intermediate abundance species from the plurality of nucleic acid molecules. In some embodiments, the methods and compositions disclosed herein can reduce the content of one or more high abundance species from the plurality of nucleic acid molecules while keeping at least at least 50%, at least 60%, at least 70%, at least 80%, at least 90%, at least 95%, or 100% of each of the one or more low abundance species. In some embodiments, the methods and compositions disclosed herein can reduce the content of one or more high abundance species from the plurality of nucleic acid molecules while keeping at least at least 50%, at least 60%, at least 70%, at least 80%, at least 90%, at least 95%, or 100% of at least one of the one or more of low abundance species. In some embodiments, the methods and compositions disclosed herein can reduce the content of one or more high abundance species from the plurality of nucleic acid molecules while keeping at least at least 50%, at least 60%, at least 70%, at least 80%, at least 90%, at least 95%, or 100% of the total of low abundance species. In some embodiments, the methods and compositions disclosed herein can reduce the content of one or more high abundance species from the plurality of nucleic acid molecules while keeping at least at least 50%, at least 60%, at least 70%, at least 80%, at least 90%, at least 95%, or 100% of at least one of the one or more of intermediate abundance species. In some embodiments, the methods and compositions disclosed herein can reduce the content of one or more high abundance species from the plurality of nucleic acid molecules while keeping at least at least 50%, at least 60%, at least 70%, at least 80%, at least 90%, at least 95%, or 100% of the total of intermediate abundance species. In some embodiments, the methods and compositions disclosed herein can reduce the content of one or more high abundance species from the plurality of nucleic acid molecules while keeping at least 50%, at least 60%, at least 70%, at least 80%, at least 90%, at least 95%, or 100% of each of the intermediate abundance species from the plurality of nucleic acid molecules.

Plurality of Nucleic Acid Molecules

The plurality of nucleic acid molecules disclosed herein can comprise a variety of nucleic acid molecules. In some embodiments, the plurality of nucleic acid molecules can comprise, DNA molecules, RNA molecules, genomic DNA molecules, cDNA molecules, mRNA molecules, rRNA molecules, siRNA molecules, or a combination thereof, and can be double-stranded or single-stranded. In some embodiments, the plurality of nucleic acid molecules comprise at least 100, at least 1,000, at least 10,000, at least 20,000, at least 30,000, at least 40,000, at least 50,000, at least 100,000, at least 1,000,000, or more species. In some embodiments, the plurality of nucleic acid molecules can be from a sample, such as a single cell, or a plurality of cells. In some embodiments, the plurality of nucleic acid molecules can be pooled from a plurality of samples, such as a plurality of single cells.

In some embodiments, the plurality of nucleic acid molecules comprises an unnormalized nucleic acid library, a partially normalized nucleic acid library, or a nucleic acid library that has been normalized by other methods, such as a cDNA library, a genomic DNA library, or the like. In some embodiments, the plurality of nucleic acid molecules can comprise a pooled unnormalized nucleic acid library, such as a pooled unnormalized nucleic acid library constructed from a plurality of unnormalized nucleic acid libraries each representing a single cell. In some embodiments, the unnormalized nucleic acid library is a cDNA library. In some embodiments, the unnormalized nucleic acid library is a genomic library. In some embodiments, the unnormalized nucleic acid library is a single-cell nucleic acid library. As used herein, a "single-cell nucleic acid library" means a collection of nucleic acid molecules, such as genomic DNA or mRNA molecules, that originates from a single cell. In some embodiments, a single-cell nucleic acid library can refer to collections of nucleic acid molecules originate from a plurality of single cells, wherein the nucleic acid molecules comprise a cellular label to identify the single cell from which the nucleic acid molecules originate.

In some embodiments, the plurality of nucleic acid molecules can be subjected to amplification before removing the high abundance species. For example, the plurality of nucleic acid molecules can comprise an amplified nucleic acid library. In some embodiments, the plurality of nucleic acid molecules can comprise at least 2, at least 4, at least 8, at least 16, at least 100, at least 1,000 or more copies of each nucleic acid molecules.

Binding Moiety

In some embodiments, the methods disclosed herein comprise hybridizing a plurality of first oligonucleotides comprising a binding moiety with the plurality of nuclei acid molecules. A variety of binding moieties can be used for the methods and compositions disclosed herein. For example, a binding moiety can be part of a binding pair. In some embodiments, the binding moiety can be a functional group added to the oligonucleotides. In some embodiments, the binding moiety can be biotin, streptavidin, heparin, an aptamer, a click-chemistry moiety, digoxigenin, primary amine(s), carboxyl(s), hydroxyl(s), aldehyde(s), ketone(s), or any combination thereof.

The binding moieties as disclosed herein are capable of bind to capture moieties such as capture molecules. In some embodiments, the binding moiety and capture molecule can be members of a binding pair, for example, biotin/streptavidin. The capture molecule can be immobilized on a solid support, such as a bead, a microparticle, or a nanoparticle.

In some embodiments, the first oligonucleotides can be extended to generate a plurality of complementary strands of the plurality of nucleic acid targets comprising the binding moiety. In some embodiments, a second strand can be synthesized using a primer that binds to a binding site on the complementary strands to produce double stranded nucleic acid molecules.

Reduce Content of High Abundance Species by Denaturation/Partial Reannealing

In some embodiments, reducing the content of high abundance species can comprise denaturation followed by partial reannealing of the double stranded nucleic acid molecules, followed by removing the reannealed complementary strands of the plurality of nucleic acid targets by a capture molecule immobilized on one or more solid support, wherein the capture molecules specifically bind to the binding moiety.

Denaturation can be performed by a variety of methods including heating the double stranded nucleic acid molecules, treating the double stranded nucleic acid molecules with organic solvents (e.g., DMS or formamide), changing the salt concentration of the double stranded nucleic acid molecules, and/or changing the pH of the double stranded nucleic acid molecules.

After denaturation, the single-stranded nucleic acid molecules can be partially reannealed. Partial reannealing can be performed by any method, for example, rapid cooling on ice, changing the salt concentration (e.g., reversing the salt concentration from the amount used in denaturation), and/or changing the pH (e.g., reversing the pH from the level used in denaturation), and the like.

It would be appreciated that the extent of reannealing can be adjusted according to various factors, including but not limited to, the type of the species to be removed (e.g. high abundance species and/or intermediate abundance species), the desired percentage of high abundance species to be removed, and/or the percentage of intermediate or low abundance species to be retained. Without being bound by any particular theory, it is believed that more abundant species (e.g., high abundance species) anneals faster than the species with lower abundance (e.g., intermediate and low abundance species) under the same anneal conditions. For example, by changing the temperature, salt concentration, pH, and/or duration of the reannealing step, the percentage of high abundance species to be removed, and/or the percentage of intermediate or low abundance species to be retained can be adjusted. In some embodiments, the temperature, salt concentration, pH, and/or duration of the reannealing step can be adjusted so that at least 10%, at least 20%, at least 30%, at least 40%, at least 50%, at least 60%, at least 70%, at least 80%, at least 90%, at least 95%, or at least 99% of a high abundance species reanneal. In some embodiments, the temperature, salt concentration, pH, and/or or duration of the reannealing step can be adjusted so that at least 10%, at least 20%, at least 30%, at least 40%, at least 50%, at least 60%, at least 70%, at least 80%, at least 90%, at least 95%, or 100% of the intermediate or low abundance species remain single-stranded.

FIG. 1 depicts an exemplary embodiment of the methods of the disclosure. A sample can comprise a plurality of nucleic acids. Some of the nucleic acids can be highly abundant 106 and some of the nucleic acids can be less abundant 105. The nucleic acids can be transformed into a double-stranded cDNA library 125 that is asymmetrically labeled with a binding moiety 120. For example, the nucleic acids 105/106 can be mRNA that is reverse transcribed. Second strand synthesis can be performed using a primer (e.g., gene-specific primer, or a random multimer primer) comprising the binding moiety 120, thereby generating an asymmetrically labeled double-stranded nucleic acid library 125. In another example, the nucleic acids 105/106 can be DNA. The DNA can be extended using a primer comprising the binding moiety 120, thereby generating an asymmetrically labeled double-stranded cDNA library 125. The double-stranded cDNA library can comprise highly abundant double-stranded cDNA species 116 and lowly abundant double-stranded cDNA species 115. The double-stranded cDNA library 125 can be ligated to adaptors 130/135, thereby generating an un-normalized library 125.

The double-stranded cDNA library 125 can be heat denatured, thereby separating the strands of the double-stranded cDNA. The heat denatured library can be re-annealed (e.g., partially reannealed) 140. The more abundant nucleic acids 106 can anneal faster than less abundant nucleic acids 105. Denaturing and partial reannealing can result in a mixture of species 141 comprising re-annealed double-stranded cDNAs comprising said binding moiety 142, single-stranded molecules comprising said binding moiety 143 and single-stranded molecules lacking said binding moiety 144.

The denatured and re-annealed library can be contacted to a solid support 145. The solid support can comprise a capture moiety that can bind to the binding moiety 120 of the asymmetrically labeled double-stranded cDNAs 115/116. Nucleic acids comprising the binding moiety 120 can be bound by the solid support. These nucleic acids can include re-annealed double-stranded cDNAs comprising said binding moiety 142, single-stranded molecules comprising said binding moiety 143. A magnet can be used to remove the solid support 145 bound to nucleic acids.

The left behind nucleic acids 150 represent the complement of the species that did not anneal (e.g., this is the complement of a single-stranded that comprised the binding moiety and was removed by the solid support, but was at a concentration low enough such that it did not anneal with that single-stranded molecule). The left behind nucleic acids 150 may not contain the binding moiety 120. The left behind nucleic acids 150 can be amplified and/or ligated with an adaptor for sequencing. These nucleic acids represent a normalized library. In some instances, library normalization may not require the use of enzymology to normalize the library (e.g., nucleases).

Methods of Library Normalization

The disclosure provides for methods for library normalization. The methods of the disclosure can be performed on a nucleic acid sample. The nucleic acid sample can comprise nucleic acids. The sample can be from a sample of the disclosure. The sample can be a single cell (e.g., the nucleic acid sample can be nucleic acids from a single cell). The nucleic acid sample can comprise RNA, DNA, or both RNA and DNA. The nucleic acids of the sample can be single stranded, double-stranded, or a mixture of both singles-stranded and double-stranded. In some instances, all or most of the nucleic acids of the sample are single stranded.

The nucleic acid sample can comprise nucleic acid targets (i.e., nucleic acid species, used interchangeably herein with nucleic acid targets) of varying abundances. For example, the nucleic acid sample can comprise high abundance targets (e.g., Actin, GapDH, globins, housekeeping genes). The nucleic acid sample can comprise low abundance targets (e.g., rare targets from stem cells or circulating tumor cells (CTCs), or lowly expressed genes). The nucleic acid sample can comprise a mixture of high abundance and low abundance targets.

Nucleic acids of the sample can be contacted with a primer comprising a binding moiety to generate a double-stranded cDNA. In some embodiments, the nucleic acid can be an RNA and the primer can be a reverse transcription primer. The reverse transcription primer can reverse transcribe the RNA, thereby generating an RNA-cDNA hybrid (e.g., first strand synthesis). A second strand can be generated using standard second strand synthesis techniques. The first cDNA strand can comprise the binding moiety. The second strand can be the complement of the first strand. The second strand may not comprise the binding moiety. This cDNA can be referred to as an asymmetrically labeled cDNA (e.g., one strand of the cDNA is labeled with the binding moiety).

When the nucleic acids of the sample are DNA, a primer comprising a binding moiety can be contacted to the nucleic acids to generate a first strand (e.g., complementary strand to the DNA template). The first strand can comprise the binding moiety. In some instances, the primer can generate a second strand that is complementary to the first strand. The second strand may not comprise the binding moiety.

With either an RNA or DNA starting template, the result can be an asymmetrically labelled double-stranded cDNA molecule where one of the strands comprises a binding moiety, and the other strand is the complement. A group of asymmetrically labeled double-stranded cDNA molecules can be referred to as an un-normalized library.

Figure 3:
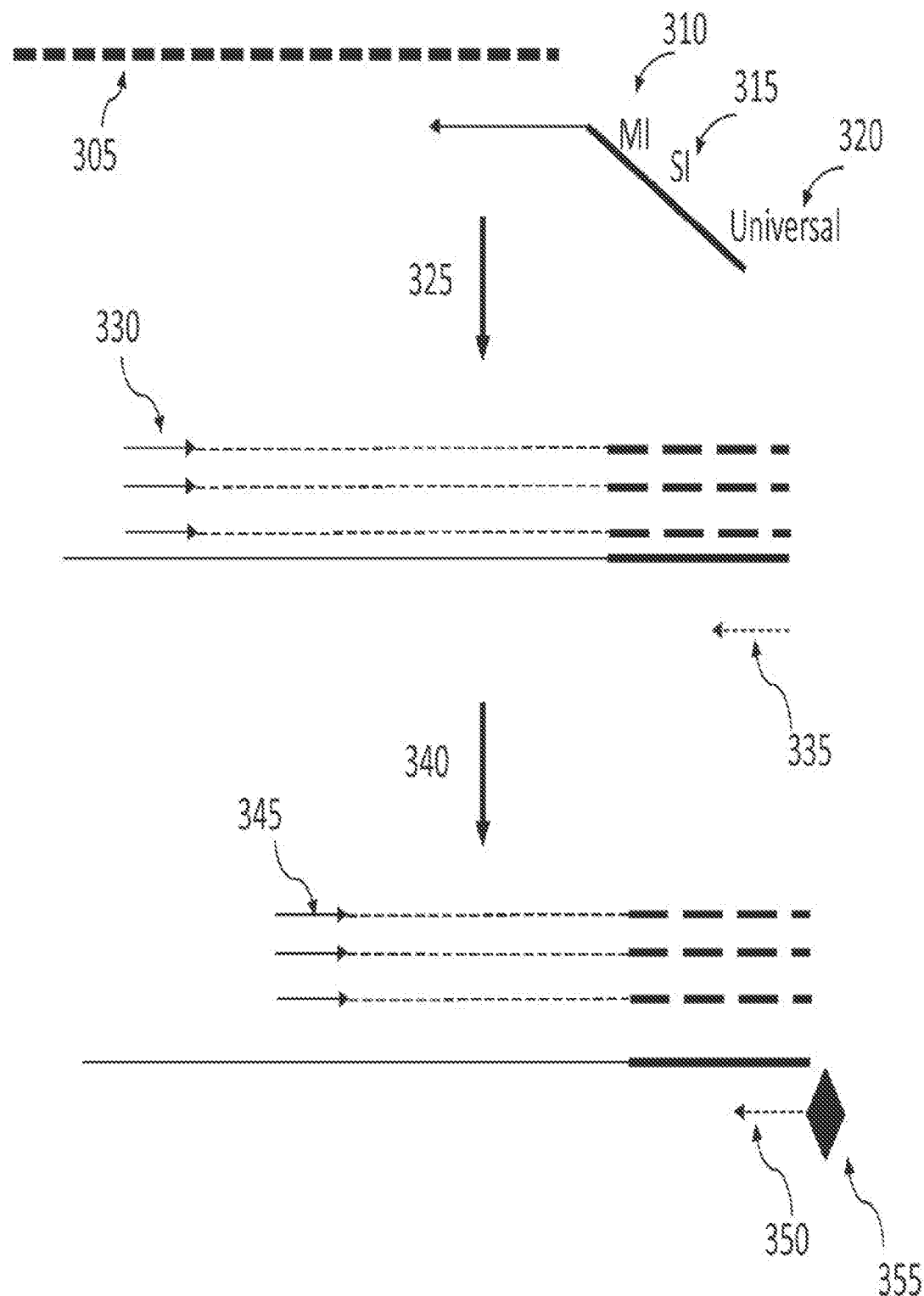
FIG. 3 illustrates an exemplary embodiment of the amplification method of the disclosure to asymmetrically label an amplicon with a binding moiety.

In some embodiments, the binding moiety is added through amplification reactions that occur after generation of the library (e.g., first strand, second strand, adaptor ligation). As shown in FIG. 3, a nucleic acid (e.g., mRNA, DNA) 305 can be reverse transcribed or extended with a primer comprising a molecular label (i.e., molecular index) 310, a sample label (i.e., cellular label, sample index) 315, and a universal label (i.e., universal primer binding sequence) 320. The product can undergo a first nested PCR amplification reaction 325 wherein a nested gene-specific primer 330 and a universal primer 335 that binds to the universal label 320 are used to amplify the product, thereby generating amplicons. In some instances, the amplicons can undergo a second round of amplification using a nested PCR primer 345 and a universal primer 350 comprising a binding moiety 355 that binds to the universal label 320. The amplification reaction can produce amplicons (e.g., nested PCR amplicons) asymmetrically labeled with a binding moiety. FIG. 3 depicts a representative amplification scheme for adding binding moiety. The binding moiety can be added at any step, such as at reverse transcription, at second strand synthesis, before adaptor ligation, after adaptor ligation, and/or at any PCR amplification step. The primer comprising the binding moiety can be used in multiple steps of a library preparation scheme.

The binding moiety can be any small molecule that has a binding partner. Exemplary binding moieties include, biotin, streptavidin, heparin, an aptamer, a click-chemistry moiety, a protein binding segment or structure, and a nucleic acid binding segment or structure, and the likes.

Figure 5A:
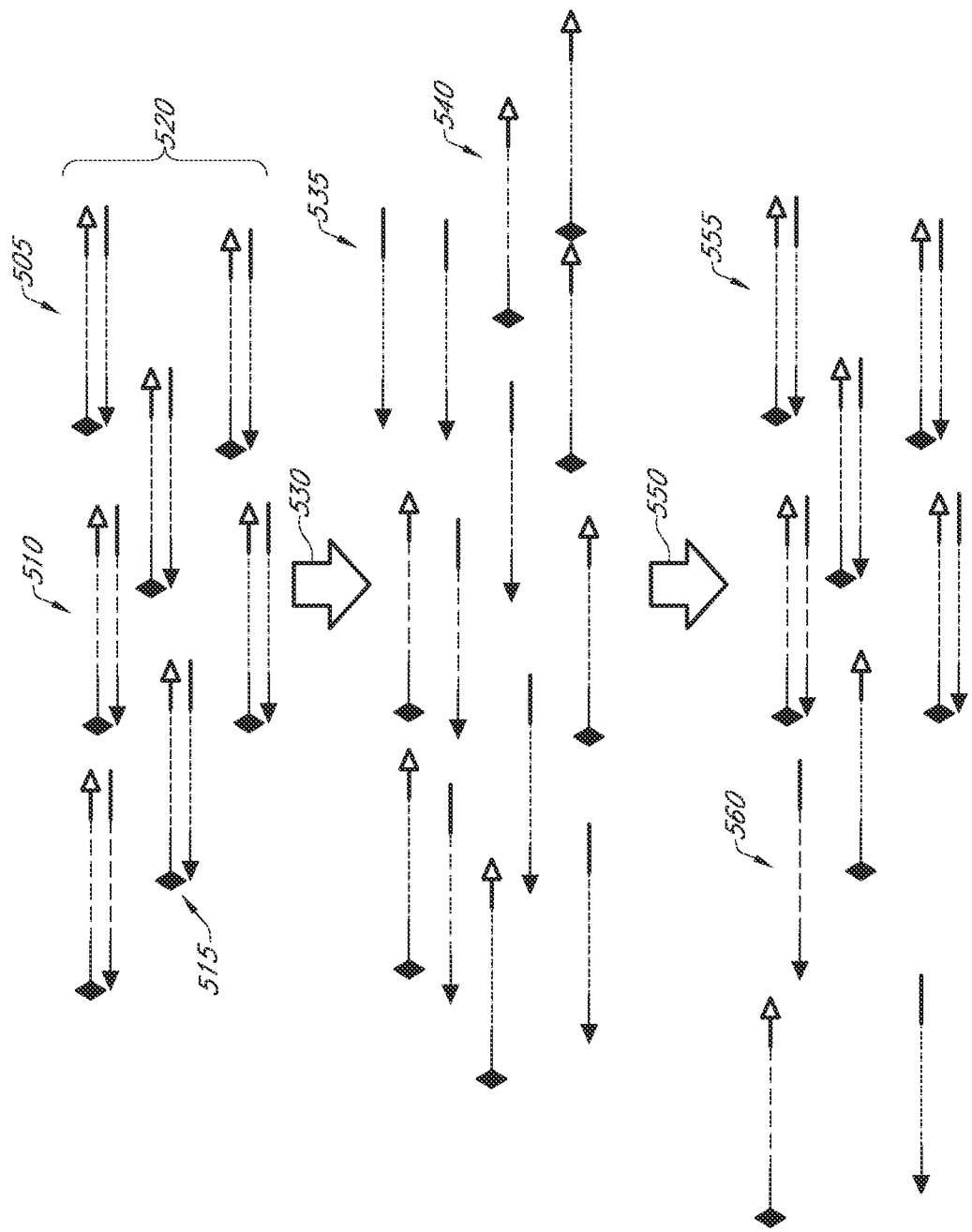
FIGS. 5A and 5B depict an exemplary embodiment of a method for adding a stochastic barcode to a target using a universal adaptor primer.
Figure 5B:
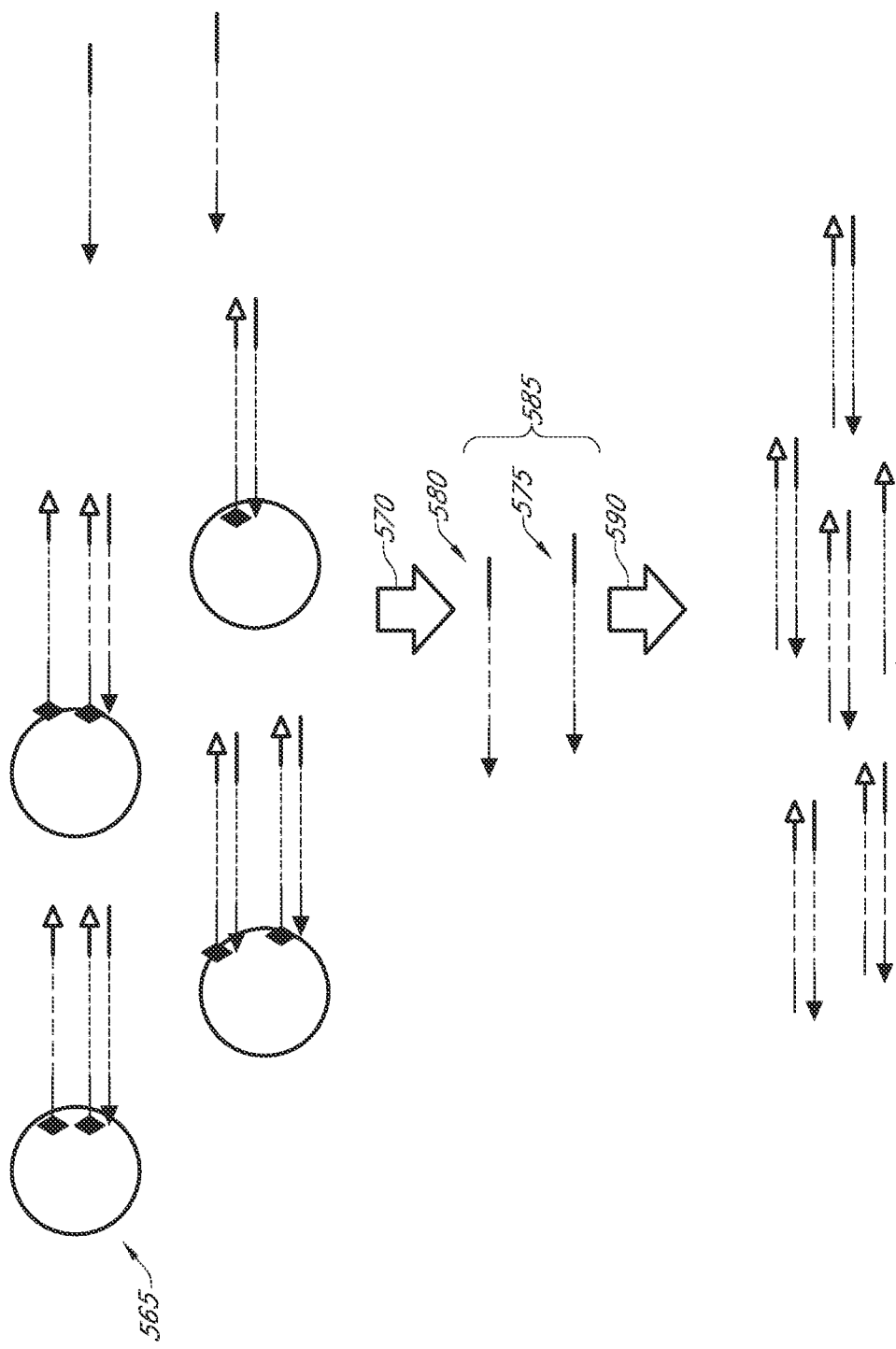

Methods and compositions described herein address the challenges of physical and enzymatic separation of ssDNA and dsDNA fractions during library normalization. As shown in FIGS. 5A and 5B, an unnormalized library 500 contains a high abundance species 505 and a low abundance species 510. During initial library preparation, the library, or a fraction of the library, is asymmetrically labeled on one end with a binding moiety 515 (such as biotin, etc.). The labeled double stranded nucleic acid molecules 520 are denatured 530 to generate single-stranded nucleic acid molecules including a high abundance species 535 and a low abundance species 540. The single-stranded nucleic acid molecules are partially reannealed 550 to form double-stranded molecules of the high abundance species 555 whereas the low abundance species remain single-stranded 560. After denaturation and partial reannealing, all of the labeled strands are captured on a support matrix 565, such as paramagnetic streptavidin beads, and the bound and unbound fractions are separated 570. Highly abundant sequences will have predominantly rehybridized, and both strands will be removed in the bound fraction. However, low abundance sequences will not have reannealed, so the complement of the labeled strand will be present in the unbound fraction. The unbound fraction including single-stranded high abundance species 575 and single-stranded low abundance species 580 would represent a normalized library 585, and could either be used directly or further amplified 590 for downstream applications.

Denaturation and Partial Re-Annealing

The un-normalized library (e.g., comprising nucleic acid target cDNAs) can be denatured. Denaturation can be performed by a variety of methods including heating the sample, treating the sample with organic solvents (e.g., DMS or formamide), changing the salt concentration of the sample, and/or changing the pH of the sample.

In some instances, denaturation is performed by heating the sample. Denaturation can be performed at a temperature of at least 50° C., 60° C., 70° C., 80° C., 90° C., or 95° C. or more. Denaturation can be performed at a temperature of at most 50° C., 60° C., 70° C., 80° C., 90° C., or 95° C. or more. Denaturation can be performed for at least 1, 2, 3, 4, 5, 6, 7, 8, 9, or 10 or more minutes. Denaturation can be performed for at most 1, 2, 3, 4, 5, 6, 7, 8, 9, or 10 or more minutes. Denaturation can result in denaturation of at least 50, 60, 70, 80, 90, or 100% of the cDNAs. Denaturation can result in denaturation of at most 50, 60, 70, 80, 90, or 100% of the cDNAs. Denaturation can result in at least 50, 60, 70, 80, 90, or 100% of nucleic acids being in single-stranded form.

The denatured sample can be re-annealed. The denatured sample can be partially re-annealed. Partial re-annealing can be performed by any method, for example, rapid cooling on ice, changing the salt concentration (e.g., reversing the salt concentration from the amount used in denaturation), and/or changing the pH (e.g., reversing the pH from the level used in denaturation), and the like. In some instances, partial re-annealing comprises cooling the denatured sample (e.g., on ice). Partial re-annealing can comprise re-annealing of at least 10, 20, 30, 40, 50, 60, 70, 80, 90 or 100% of the strands of the denatured sample. Partial re-annealing can comprise re-annealing of at most 10, 20, 30, 40, 50, 60, 70, 80, 90 or 100% of the strands of the denatured sample. At least 10, 20, 30, 40, 50, 60, 70, 80, 90 or 100% of strands from highly abundant nucleic acids can be re-annealed during the step of partial re-annealing. At most 10, 20, 30, 40, 50, 60, 70, 80, 90 or 100% of strands from highly abundant nucleic acids can be re-annealed during the step of partial re-annealing. At least 10, 20, 30, 40, 50, 60, 70, 80, 90 or 100% of strands from lower abundant nucleic acids can be re-annealed during the step of partial re-annealing. At most 10, 20, 30, 40, 50, 60, 70, 80, 90 or 100% of strands from lower abundant nucleic acids can be re-annealed during the step of partial re-annealing.

Strands from higher abundant species can re-anneal at least 50, 100, 150, 200, 250, 300, 350, 400, 450, or 500% or more quickly than strands from lower abundant species. Strands from higher abundant species can re-anneal at most 50, 100, 150, 200, 250, 300, 350, 400, 450, or 500% or more quickly than strands from lower abundant species. Strands from higher abundant species can re-anneal at least 1, 2, 3, 4, 5, 6, 7, 8, 9, or 10-fold or more than strands from lower abundant species. Strands from higher abundant species can re-anneal at most 1, 2, 3, 4, 5, 6, 7, 8, 9, or 10-fold or more than strands from lower abundant species.

After re-annealing the sample can comprise a plurality of double-stranded molecules, a plurality of single-stranded molecules comprising a binding moiety, and a plurality of single-stranded molecules that may not comprise the binding moiety. The double-stranded molecules can comprise one strand that can comprise the binding moiety and one strand that does not comprise the binding moiety.

The re-annealed sample can be contacted with a solid support. The solid support can comprise a capture moiety. A capture moiety can bind to the binding moiety. For example, if the binding moiety is biotin, the capture moiety can be streptavidin. The solid support can be, for example, a resin, a slurry, a bead, a resin, a hydrogel, a semi-solid support, an insoluble support, and/or a semi-solid support. In some instances, the solid support is a resin.

The solid support can have a physical property. For example, the solid support can be soluble in certain pH conditions, salt conditions, and/or temperature conditions. The solid support can be magnetic, ferromagnetic, and/or paramagnetic.

The solid support can bind to the molecules of the re-annealed samples that comprise the binding moiety. The solid support can bind to double-stranded cDNAs (e.g., comprising the binding moiety). The solid support can bind to single-stranded un-annealed strands (e.g., comprising the binding moiety).

The solid support can used to purify the sample. The solid support can be separated from the sample (i.e., supernatant) (e.g., by centrifugation, magnetism). The leftover sample (i.e., supernatant) can be referred to as a normalized library. The normalized library can comprise single-stranded nucleic acid molecules that may not comprise a binding moiety. The single-stranded nucleic acid molecules can be molecules that did not anneal during the partial re-annealing step of the method.

The normalized library can comprise relatively more equal amount of lower and higher abundant species compared to an un-normalized library. For example, higher abundant species can be at least 1, 2, 3, 4, 5, 6, 7, 8, 9, 10, 11, 12, 13, 14, 15, 16, 17, 18, 19, or 20 or more times greater than lower abundant species in a normalized library compared to an un-normalized library. Higher abundant species can be at most 1, 2, 3, 4, 5, 6, 7, 8, 9, 10, 11, 12, 13, 14, 15, 16, 17, 18, 19, or 20 or more times greater than lower abundant species in a normalized library compared to an un-normalized library. Lower abundant species can be at least 1, 2, 3, 4, 5, 6, 7, 8, 9, 10, 11, 12, 13, 14, 15, 16, 17, 18, 19, or 20 or more times greater than higher abundant species in a normalized library compared to an un-normalized library. Lower abundant species can be at most 1, 2, 3, 4, 5, 6, 7, 8, 9, 10, 11, 12, 13, 14, 15, 16, 17, 18, 19, or 20 or more times greater than higher abundant species in a normalized library compared to an un-normalized library.

Use of Blockers

In some embodiments, the methods of the disclosure provide for the use of blockers during denaturation and partial re-annealing. As used herein, blockers refer to oligonucleotide sequences that can hybridize to the universal sequences of a library (e.g., universal primer sequences, universal sequencing flow cell sequences). The blockers can be used to prevent targets/amplicons from different genes annealing together during partial re-annealing through their universal regions without taking into account the gene sequence.

Figure 4:
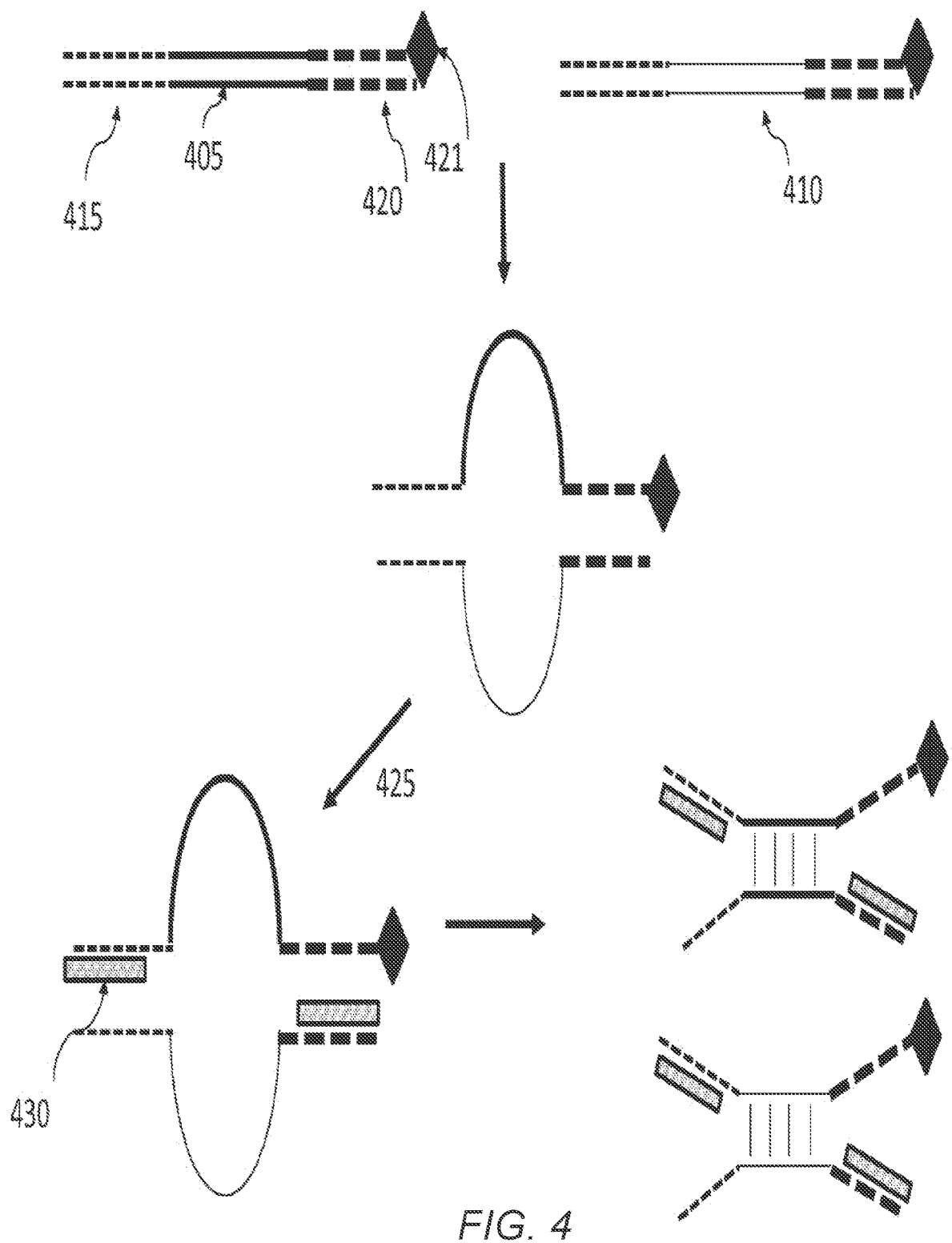
FIG. 4 illustrates an exemplary embodiment of the use of blockers in the methods of the disclosure.

An exemplary use of blockers is shown in FIG. 4. A first target 405 and a second target 410 can each comprise universal sequences 415/420 and a binding moiety 421. In some instances, during denaturation and partial re-annealing targets with difference sequences 405/410 can anneal together through the universal sequences that each of them comprise 415/420. Blockers can be used to prevent this from happening. The sample can be contacted 425 with blockers 430. The blockers 430 can hybridize to one or more universal sequences of the targets. One or more different types of blockers 430 can be used. The blockers can aid partial re-annealing by forcing strands to associate (e.g., hybridize) through their gene sequences. In this way, blockers can be used to aid library normalization methods of the disclosure.

A blocker can be at least 1, 2, 3, 4, 5, 6, 7, 8, 9, or 10 or more nucleotides in length. A blocker can be at most 1, 2, 3, 4, 5, 6, 7, 8, 9, or 10 or more nucleotides in length. A blocker can hybridize to its target with at least 10, 20, 30, 40, 50, 60, 70, 80, 90 or 100% complementarity. A blocker can hybridize to its target with at most 10, 20, 30, 40, 50, 60, 70, 80, 90 or 100% complementarity.

In some embodiments, the library normalization methods of the disclosure can be performed on a solid support. For example, a library can be generated wherein the amplicons of the library are asymmetrically labeled with one of the molecules involved in click chemistry (e.g., azide, alkyne, for the azide-alkyne cycloaddition). The solid support can comprise the other molecule in the click chemistry. For example, the amplicon can comprise an alkyne and the solid support can comprise an azide. The amplicons can be attached to the solid support (e.g., by click chemistry). The solid support can be heated thereby inducing denaturation of the attached amplicons. During partial re-annealing the amplicons that are more abundant can re-anneal to the molecules attached to the solid support. The amplicons that are less abundant can be left in solution (e.g., by centrifugation, magnetism, chromatography). The solid supports can be removed from the solution, thereby leaving by a normalized library.

Amplification

One or more nucleic acid amplification reactions may be performed to create multiple copies of the normalized target nucleic acid molecules. Amplification may be performed in a multiplexed manner, wherein multiple target nucleic acid sequences are amplified simultaneously. The amplification reaction may be used to add sequencing adaptors to the nucleic acid molecules. The amplification reactions may comprise amplifying at least a portion of a sample label, if present. The amplification reactions may comprise amplifying at least a portion of the cellular and/or molecular label. The amplification reactions may comprise amplifying at least a portion of a sample tag, a cellular label, a spatial label, a molecular label, a target nucleic acid, or a combination thereof. The amplification reactions may comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids. The method may further comprise conducting one or more cDNA synthesis reactions to produce one or more cDNA copies of target-barcode molecules comprising a sample label, a cellular label, a spatial label, and/or a molecular label.

In some embodiments, amplification may be performed using a polymerase chain reaction (PCR). As used herein, PCR may refer to a reaction for the in vitro amplification of specific DNA sequences by the simultaneous primer extension of complementary strands of DNA. As used herein, PCR may encompass derivative forms of the reaction, including but not limited to, RT-PCR, real-time PCR, nested PCR, quantitative PCR, multiplexed PCR, digital PCR, and assembly PCR.

Amplification of the labeled nucleic acids can also comprise non-PCR based methods. Examples of non-PCR based methods include, but are not limited to, multiple displacement amplification (MDA), transcription-mediated amplification (TMA), whole transcriptome amplification (WTA), whole genome amplification (WGA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some instances, the amplification may not produce circularized transcripts.

Suppression PCR can be used for amplification methods of the disclosure. Suppression PCR can refer to the selective exclusion of molecules less than a certain size flanked by terminal inverted repeats, due to their inefficient amplification when the primer(s) used for amplification correspond(s) to the entire repeat or a fraction of the repeat. The reason for this can lie in the equilibrium between productive PCR primer annealing and nonproductive self-annealing of the fragment's complementary ends. At a fixed size of a flanking terminal inverted repeat, the shorter the insert, the stronger the suppression effect and vice versa. Likewise, at a fixed insert size, the longer the terminal inverted repeat, the stronger the suppression effect.

Suppression PCR can use adapters that are ligated to the end of a DNA fragment prior to PCR amplification. Upon melting and annealing, single-stranded DNA fragments having self-complementary adapters at the 5'- and 3'-ends of the strand can form suppressive "tennis racquet" shaped structures that suppress amplification of the fragments during PCR.

In some instances, the methods disclosed herein further comprise conducting a polymerase chain reaction on the labeled nucleic acid (e.g., labeled-RNA, labeled-DNA, labeled-cDNA) to produce a stochastically labeled-amplicon. The stochastically labeled-amplicon may be a double-stranded molecule. The double-stranded molecule may comprise or be a double-stranded RNA molecule, a double-stranded DNA molecule, or a RNA molecule hybridized to a DNA molecule. One or both of the strands of the double-stranded molecule may comprise a sample label, a spatial label, a cellular label, and/or a molecular label. The stochastically labeled-amplicon can be a single-stranded molecule. The single-stranded molecule may comprise DNA, RNA, or a combination thereof. The nucleic acids of the disclosure may comprise synthetic or altered nucleic acids.

Amplification may comprise use of one or more non-natural nucleotides. Non-natural nucleotides may comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides may be added to one or more cycles of an amplification reaction. The addition of the non-natural nucleotides may be used to identify products as specific cycles or time points in the amplification reaction.

Conducting the one or more amplification reactions may comprise the use of one or more primers. The one or more primers may comprise at least 1, 2, 3, 4, 5, 6, 7, 8, 9, 10, 11, 12, 13, 14, or 15 or more nucleotides. The one or more primers may comprise at least 1, 2, 3, 4, 5, 6, 7, 8, 9, 10, 11, 12, 13, 14, or 15 or more nucleotides. The one or more primers may comprise less than 12-15 nucleotides. The one or more primers may anneal to at least a portion of the plurality of stochastically labeled targets. The one or more primers may anneal to the 3' end or 5' end of the plurality of stochastically labeled targets. The one or more primers may anneal to an internal region of the plurality of stochastically labeled targets. The internal region may be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of stochastically labeled targets. The one or more primers may comprise a fixed panel of primers. The one or more primers may comprise at least one or more custom primers. The one or more primers may comprise at least one or more control primers. The one or more primers may comprise at least one or more gene-specific primers.

The one or more primers may comprise any universal primer of the disclosure. The universal primer may anneal to a universal primer binding site. The one or more custom primers may anneal to a first sample label, a second sample label, a spatial label, a cellular label, a molecular label, a target, or any combination thereof. The one or more primers may comprise a universal primer and a custom primer. The custom primer may be designed to amplify one or more targets. The targets may comprise a subset of the total nucleic acids in one or more samples. The targets may comprise a subset of the total stochastically labeled targets in one or more samples. The one or more primers may comprise at least 96 or more custom primers. The one or more primers may comprise at least 960 or more custom primers. The one or more primers may comprise at least 9600 or more custom primers. The one or more custom primers may anneal to two or more different labeled nucleic acids. The two or more different labeled nucleic acids may correspond to one or more genes.

Any amplification scheme can be used in the methods of the present disclosure. For example, in one scheme, the first round PCR can amplify molecules (e.g., attached to the bead) using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and molecular index on read 1, the gene on read 2, and the sample index on index 1 read.

Amplification can be performed in one or more rounds. In some instances there are multiple rounds of amplification. Amplification can comprise two or more rounds of amplification. The first amplification can be an extension off X' to generate the gene specific region. The second amplification can occur when a sample nucleic hybridizes to the newly generated strand.

In some embodiments hybridization does not need to occur at the end of a nucleic acid molecule. In some embodiments a target nucleic acid within an intact strand of a longer nucleic acid is hybridized and amplified. For example a target within a longer section of genomic DNA or mRNA. A target can be more than 50 nt, more than 100 nt, or more that 1000 nt from an end of a polynucleotide.

Library Preparation Including Adaptor Ligation

The single-stranded molecules of the un-normalized library (or normalized library) can be prepared for sequencing, which can, for example, include generation of a double-stranded molecule and incorporation of flow cell sequencing adaptors (e.g., by ligation and/or hybridization and PCR).

In some embodiments, adaptors can be ligated to the double-stranded nucleic acid. Adaptors can comprise a first universal primer sequence of the disclosure, a second universal primer sequence of the disclosure, and a restriction endonuclease binding site, or any combination thereof. In some instances, the adaptor comprises a second universal primer sequence of the disclosure and a restriction endonuclease binding site.

The term "adaptor" used herein refers to a single-stranded, or double-stranded oligonucleotide of at least 10, 15, 20 or 25 bases that may be attached to the end of a nucleic acid. Adaptor sequences may be synthesized using for example, priming sites, the complement of a priming site, and recognition sites for endonucleases, common sequences and promoters. The adaptor may be entirely or substantially double stranded. A double stranded adaptor may comprise two oligonucleotides that are at least partially complementary. The adaptor may be phosphorylated or unphosphorylated on one or both strands. The adaptor can have a double stranded section and a single stranded overhang section that is completely or partially complementary to an overhang (e.g., generated by a restriction enzyme, or a polymerase enzyme). The overhang in the adaptor may be, for example, 4 to 8 bases. For example, when DNA is digested with the restriction enzyme EcoRI the resulting double stranded fragments are flanked at either end by the single stranded overhang 5'-AATT-3', an adaptor that carries a single stranded overhang 5'-AATT-3' can hybridize to the fragment through complementarity between the overhanging regions. This "sticky end" hybridization of the adaptor to the fragment facilitates ligation of the adaptor to the fragment, however, blunt ended ligation is also possible. Blunt ends can be converted to sticky ends using, for example, the exonuclease activity of the Klenow fragment. For example when DNA is digested with PvuII the blunt ends can be converted to a two base pair overhang by incubating the fragments with Klenow in the presence of dTTP and dCTP. Overhangs may also be converted to blunt ends by filling in an overhang or removing an overhang.

Adaptors may be ligated to double-stranded cDNAs of the disclosure. Ligation methods can include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3' to 5' phosphodiester bond, substrates include single-stranded RNA and DNA as well as dinucleoside pyrophosphates; or any other methods described in the art. Different enzymes generate different overhangs and the overhang of the adaptor can be targeted to ligate to fragments generated by selected restriction enzymes.

In some embodiments, a double stranded adaptor is used and only one strand of the adaptor is ligated to the double-stranded cDNA. Ligation of one strand of an adaptor may be selectively blocked. To block ligation, for example, one strand of the adaptor can be designed to introduce a gap of one or more nucleotides between the 5' end of that strand of the adaptor and the 3' end of the target nucleic acid. Absence of a phosphate from the 5' end of an adaptor can block ligation of that 5' end to an available 3'OH.

Sequencing

Determining the number of different stochastically labeled nucleic acids may comprise determining the sequence of the labeled target, the spatial label, the molecular label, the sample label, and the cellular label or any product thereof (e.g. labeled-amplicons, labeled-cDNA molecules). An amplified target may be subjected to sequencing. Determining the sequence of the stochastically labeled nucleic acid or any product thereof may comprise conducting a sequencing reaction to determine the sequence of at least a portion of a sample label, a spatial label, a cellular label, a molecular label, and/or at least a portion of the stochastically labeled target, a complement thereof, a reverse complement thereof, or any combination thereof.

Determination of the sequence of a nucleic acid (e.g. amplified nucleic acid, labeled nucleic acid, cDNA copy of a labeled nucleic acid, etc.) may be performed using variety of sequencing methods including, but not limited to, sequencing by synthesis (SBS) sequencing by hybridization (SBH), sequencing by ligation (SBL), quantitative incremental fluorescent nucleotide addition sequencing (QIF-NAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, or single template molecule OLA using a ligated circular padlock probe and a rolling circle amplification (RCA) readout), and the like.

In some instances, determining the sequence of the labeled nucleic acid or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the labeled nucleic acid or any product thereof may be determined by electron microscopy or a chemical-sensitive field effect transistor (chemFET) array.

High-throughput sequencing methods, such as cyclic array sequencing using platforms such as Roche 454, Illumina Solexa, ABI-SOLiD, ION Torrent, Complete Genomics, Pacific Bioscience, Helicos, or the Polonator platform, may also be utilized. Sequencing may comprise MiSeq sequencing. Sequencing may comprise HiSeq sequencing.

The stochastically labeled targets can comprise nucleic acids representing from about 0.01% of the genes of an organism's genome to about 100% of the genes of an organism's genome. For example, about 0.01% of the genes of an organism's genome to about 100% of the genes of an organism's genome can be sequenced using a target complimentary region comprising a plurality of multimers by capturing the genes containing a complimentary sequence from the sample. In some embodiments, the labeled nucleic acids comprise nucleic acids representing from about 0.01% of the transcripts of an organism's transcriptome to about 100% of the transcripts of an organism's transcriptome. For example, about 0.501% of the transcripts of an organism's transcriptome to about 100% of the transcripts of an organism's transcriptome can be sequenced using a target complimentary region comprising a poly-T tail by capturing the mRNAs from the sample.

Sequencing may comprise sequencing at least about 10, 20, 30, 40, 50, 60, 70, 80, 90, 100 or more nucleotides or base pairs of the labeled nucleic acid and/or stochastic barcode. Sequencing may comprise sequencing at most about 10, 20, 30, 40, 50, 60, 70, 80, 90, 100 or more nucleotides or base pairs of the labeled nucleic acid and/or stochastic barcode. Sequencing can comprise sequencing at least about 200, 300, 400, 500, 600, 700, 800, 900, 1,000 or more nucleotides or base pairs of the labeled nucleic acid and/or stochastic barcode. Sequencing can comprise sequencing at most about 200, 300, 400, 500, 600, 700, 800, 900, 1,000 or more nucleotides or base pairs of the labeled nucleic acid and/or stochastic barcode. Sequencing can comprise sequencing at least about 1,500; 2,000; 3,000; 4,000; 5,000; 6,000; 7,000; 8,000; 9,000; or 10,000 or more nucleotides or base pairs of the labeled nucleic acid and/or stochastic barcode. Sequencing can comprise sequencing at most about 1,500; 2,000; 3,000; 4,000; 5,000; 6,000; 7,000; 8,000; 9,000; or 10,000 or more nucleotides or base pairs of the labeled nucleic acid and/or stochastic barcode.

Sequencing may comprise at least about 200, 300, 400, 500, 600, 700, 800, 900, 1,000 or more sequencing reads per run. Sequencing may comprise at most about 200, 300, 400, 500, 600, 700, 800, 900, 1,000 or more sequencing reads per run. In some instances, sequencing comprises sequencing at least about 1,500; 2,000; 3,000; 4,000; 5,000; 6,000; 7,000; 8,000; 9,000; or 10,000 or more sequencing reads per run. In some instances, sequencing comprises sequencing at most about 1,500; 2,000; 3,000; 4,000; 5,000; 6,000; 7,000; 8,000; 9,000; or 10,000 or more sequencing reads per run. Sequencing can comprise sequencing at least 10, 50, 100, 150, 200, 250, 300, 350, 400, 450, 500, 550, 600, 650, 700, 750, 800, 850, 900, 950 or 1000 or more millions of sequencing reads per run. Sequencing can comprise sequencing at most 10, 50, 100, 150, 200, 250, 300, 350, 400, 450, 500, 550, 600, 650, 700, 750, 800, 850, 900, 950 or 1000 or more millions of sequencing reads per run. Sequencing can comprise sequencing at least 100, 200, 300, 400, 500, 600, 700, 800, 900, 1000, 1100, 1200, 1300, 1400, 1500, 1600, 2000, 3000, 4000, or 5000 or more millions of sequencing reads in total. Sequencing can comprise sequencing at most 100, 200, 300, 400, 500, 600, 700, 800, 900, 1000, 1100, 1200, 1300, 1400, 1500, 1600, 2000, 3000, 4000, or 5000 or more millions of sequencing reads in total. Sequencing may comprise less than or equal to about 1,600,000,000 sequencing reads per run. Sequencing may comprise less than or equal to about 200,000,000 reads per run.

In the normalized library generated by the methods of the disclosure, less abundant (e.g., rarer) transcripts can be identified more easily than in an un-normalized library. Sequencing reads of less abundant transcripts in a normalized library can comprise a larger portion of total reads of than in an un-normalized library. Sequencing reads of a less abundant transcript in a normalized library can comprise at least 50, 100, 150, 200, 250, 300, 350, 400, 450 or 500% or more reads compared to reads of the same transcript in an un-normalized library. Sequencing reads of a less abundant transcript in a normalized library can be at least 1, 2, 3, 4, 5, or 6 or more fold than sequencing reads for the same transcript in an un-normalized library.

Stochastic Barcodes

A stochastic barcode used herein refers to a polynucleotide sequence that may be used to stochastically label (e.g., barcode, tag) a target. A stochastic barcode can comprise one or more labels. Exemplary labels include, but not limited to, a universal label, a cellular label, a molecular label, a sample label, a plate label, a spatial label, and/or a pre-spatial label. A stochastic barcode can comprise a 5'amine that may link the stochastic barcode to a solid support. The stochastic barcode can comprise one or more universal labels, one or more dimension labels, one or more spatial labels, one or more cellular labels, and/or one or more molecular labels. The location of each of the various labels in the stochastic barcode can vary. For example, the universal label may be 5'-most label. The molecular label may be the 3'-most label. The spatial label, dimension label, and the cellular label may be in any order. In some embodiments, the universal label, the spatial label, the dimension label, the cellular label, and the molecular label are in any order. The stochastic barcode can comprise a target-binding region. The target-binding region can interact with a target (e.g., target nucleic acid, RNA, mRNA, DNA) in a sample. For example, a target-binding region can comprise an oligo dT sequence which can interact with poly-A tails of mRNAs. In some instances, the labels of the stochastic barcode (e.g., universal label, dimension label, spatial label, cellular label, and molecular label) may be separated by 1, 2, 3, 4, 5, 6, 7, 8, 9, 10, 11, 12, 13, 14, 15, 16, 17, 18, 19, or 20 or more nucleotides.

A stochastic barcode may comprise one or more universal labels. The one or more universal labels may be the same for all stochastic barcodes in the set of stochastic barcodes (e.g., attached to a given solid support). In some embodiments, the one or more universal labels may be the same for all stochastic barcodes attached to a plurality of beads. In some embodiments, a universal label may comprise a nucleic acid sequence that is capable of hybridizing to a sequencing primer. Sequencing primers may be used for sequencing stochastic barcodes comprising a universal label. Sequencing primers (e.g., universal sequencing primers) may comprise sequencing primers associated with high-throughput sequencing platforms. In some embodiments, a universal label may comprise a nucleic acid sequence that is capable of hybridizing to a PCR primer. In some embodiments, the universal label may comprise a nucleic acid sequence that is capable of hybridizing to a sequencing primer and a PCR primer. The nucleic acid sequence of the universal label that is capable of hybridizing to a sequencing or PCR primer may be referred to as a primer binding site. A universal label may comprise a sequence that may be used to initiate transcription of the stochastic barcode. A universal label may comprise a sequence that may be used for extension of the stochastic barcode or a region within the stochastic barcode. A universal label may be at least about 1, 2, 3, 4, 5, 10, 15, 20, 25, 30, 35, 40, 45, 50 or more nucleotides in length. A universal label may comprise at least about 10 nucleotides. A universal label may be at most about 1, 2, 3, 4, 5, 10, 15, 20, 25, 30, 35, 40, 45, 50 or more nucleotides in length. In some embodiments, a cleavable linker or modified nucleotide may be part of the universal label sequence to enable the stochastic barcode to be cleaved off from the support. As used herein, a universal label can be used interchangeably with "universal PCR primer."

A stochastic barcode can comprise a dimension label. A dimension label can comprise a nucleic acid sequence that provides information about a dimension in which the stochastic labeling occurred. For example, a dimension label can provide information about the time at which a target was stochastically barcoded. A dimension label can be associated with a time of stochastic barcoding in a sample. A dimension label can be activated at the time of stochastic labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with stochastic barcodes at the G1 phase of the cell cycle. The cells can be pulsed again with stochastic barcodes at the S phase of the cell cycle, and so on. Stochastic barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific timepoint. The activatable dimension label may be constitutively activated (e.g., not turned off). The activatable dimension label can be reversibly activated (e.g., the activatable dimension label can be turned on and turned off). The dimension label can be reversibly activatable at least 1, 2, 3, 4, 5, 6, 7, 8, 9, or 10 or more times. The dimension label can be reversibly activatable at least 1, 2, 3, 4, 5, 6, 7, 8, 9, or 10 or more times. The dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can be identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support may comprise the same dimension label. In some embodiments, at least 60% of stochastic barcodes on the same solid support may comprise the same dimension label. In some embodiments, at least 95% of stochastic barcodes on the same solid support may comprise the same dimension label.

There may be as many as $10^6$ or more unique dimension label sequences represented in a plurality of solid supports (e.g., beads). A dimension label may be at least about 1, 2, 3, 4, 5, 10, 15, 20, 25, 30, 35, 40, 45, 50 or more nucleotides in length. A dimension label may be at most about 300, 200, 100, 90, 80, 70, 60, 50, 40, 30, 20, 15, 12, 10, 9, 8, 7, 6, 5, 4 or fewer or more nucleotides in length. A dimension label may comprise from about 5 to about 200 nucleotides. A dimension label may comprise from about 10 to about 150 nucleotides. A dimension label may comprise from about 20 to about 125 nucleotides in length.

A stochastic barcode can comprise a spatial label. A spatial label can comprise a nucleic acid sequence that provides information about the spatial orientation of a target molecule which is associated with the stochastic barcode. A spatial label can be associated with a coordinate in a sample. The coordinate can be a fixed coordinate. For example a coordinate can be fixed in reference to a substrate. A spatial label can be in reference to a two or three-dimensional grid. A coordinate can be fixed in reference to a landmark. The landmark can be identifiable in space. A landmark can a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, or a droplet). In some instances, multiple spatial labels are used together to encode one or more positions in space.

The spatial label can be identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support may comprise the same spatial label. In some embodiments, at least 60% of stochastic barcodes on the same solid support may comprise the same spatial label. In some embodiments, at least 95% of stochastic barcodes on the same solid support may comprise the same spatial label.

There may be as many as $10^6$ or more unique spatial label sequences represented in a plurality of solid supports (e.g., beads). A spatial label may be at least about 1, 2, 3, 4, 5, 10, 15, 20, 25, 30, 35, 40, 45, 50 or more nucleotides in length. A spatial label may be at most about 300, 200, 100, 90, 80, 70, 60, 50, 40, 30, 20, 15, 12, 10, 9, 8, 7, 6, 5, 4 or fewer or more nucleotides in length. A spatial label may comprise from about 5 to about 200 nucleotides. A spatial label may comprise from about 10 to about 150 nucleotides. A spatial label may comprise from about 20 to about 125 nucleotides in length.

Stochastic barcodes may comprise a cellular label (i.e., sample label). As used herein, the terms "sample label," and "cellular label" may be used interchangeably. A cellular label may comprise a nucleic acid sequence that provides information for determining which target nucleic acid originated from which cell. In some embodiments, the cellular label is identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support may comprise the same cellular label. In some embodiments, at least 60% of stochastic barcodes on the same solid support may comprise the same cellular label. In some embodiment, at least 95% of stochastic barcodes on the same solid support may comprise the same cellular label.

There may be as many as $10^6$ or more unique cellular label sequences represented in a plurality of solid supports (e.g., beads). A cellular label may be at least about 1, 2, 3, 4, 5, 10, 15, 20, 25, 30, 35, 40, 45, 50 or more nucleotides in length. A cellular label may be at most about 300, 200, 100, 90, 80, 70, 60, 50, 40, 30, 20, 15, 12, 10, 9, 8, 7, 6, 5, 4 or fewer or more nucleotides in length. A cellular label may comprise from about 5 to about 200 nucleotides. A cellular label may comprise from about 10 to about 150 nucleotides. A cellular label may comprise from about 20 to about 125 nucleotides in length.

Stochastic barcodes may comprise a molecular label. A molecular label may comprise a nucleic acid sequence that provides identifying information for the specific type of target nucleic acid species hybridized to the stochastic barcode. A molecular label may comprise a nucleic acid sequence that provides a counter for the specific occurrence of the target nucleic acid species hybridized to the stochastic barcode (e.g., target-binding region). In some embodiments, a diverse set of molecular labels are attached to a given solid support (e.g., bead). In some embodiments, there may be as many as $10^6$ or more unique molecular label sequences attached to a given solid support (e.g., bead). In some embodiments, there may be as many as $10^5$ or more unique molecular label sequences attached to a given solid support (e.g., bead). In some embodiments, there may be as many as $10^4$ or more unique molecular label sequences attached to a given solid support (e.g., bead). In some embodiments, there may be as many as $10^3$ or more unique molecular label sequences attached to a given solid support (e.g., bead). In some embodiments, there may be as many as $10^2$ or more unique molecular label sequences attached to a given solid support (e.g., bead). A molecular label may be at least about 1, 2, 3, 4, 5, 10, 15, 20, 25, 30, 35, 40, 45, 50 or more nucleotides in length. A molecular label may be at most about 300, 200, 100, 90, 80, 70, 60, 50, 40, 30, 20, 15, 12, 10, 9, 8, 7, 6, 5, 4 or fewer nucleotides in length.

Stochastic barcodes may comprise a target binding region. In some embodiments, the target binding regions may comprise a nucleic acid sequence that hybridizes specifically to a target (e.g., target nucleic acid, target molecule, e.g., a cellular nucleic acid to be analyzed), for example to a specific gene sequence. In some embodiments, a target binding region may comprise a nucleic acid sequence that may attach (e.g., hybridize) to a specific location of a specific target nucleic acid. In some embodiments, the target binding region may comprise a nucleic acid sequence that is capable of specific hybridization to a restriction site overhang (e.g. an EcoRI sticky-end overhang). The stochastic barcode may then ligate to any nucleic acid molecule comprising a sequence complementary to the restriction site overhang.

A stochastic barcode can comprise a target-binding region. A target-binding region can hybridize with a target of interest. For example, a target-binding region can comprise an oligo dT which can hybridize with mRNAs comprising poly-adenylated ends. A target-binding region can be gene-specific. For example, a target-binding region can be configured to hybridize to a specific region of a target. A target-binding region can be at least 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 or more nucleotides in length. A target-binding region can be at most 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 or more nucleotides in length. A target-binding region can be from 5-30 nucleotides in length. When a stochastic barcode comprises a gene-specific target-binding region, the stochastic barcode can be referred to as a gene-specific stochastic barcode.

A target binding region may comprise a non-specific target nucleic acid sequence. A non-specific target nucleic acid sequence may refer to a sequence that may bind to multiple target nucleic acids, independent of the specific sequence of the target nucleic acid. For example, target binding region may comprise a random multimer sequence, or an oligo-dT sequence that hybridizes to the poly-A tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all stochastic barcodes attached to a given bead. In some embodiments, the target binding regions for the plurality of stochastic barcodes attached to a given bead may comprise two or more different target binding sequences. A target binding region may be at least about 5, 10, 15, 20, 25, 30, 35, 40, 45, 50 or more nucleotides in length. A target binding region may be at most about 5, 10, 15, 20, 25, 30, 35, 40, 45, 50 or more nucleotides in length.

A stochastic barcode can comprise an orientation property which can be used to orient (e.g., align) the stochastic barcodes. A stochastic barcode can comprise a moiety for isoelectric focusing. Different stochastic barcodes can comprise different isoelectric focusing points. When these stochastic barcodes are introduced to a sample, the sample can undergo isoelectric focusing in order to orient the stochastic barcodes into a known way. In this way, the orientation property can be used to develop a known map of stochastic barcodes in a sample. Exemplary orientation properties can include, electrophoretic mobility (e.g., based on size of the stochastic barcode), isoelectric point, spin, conductivity, and/or self-assembly. For example, stochastic barcodes can comprise an orientation property of self-assembly, or can self-assemble into a specific orientation (e.g., nucleic acid nanostructure) upon activation.

A stochastic barcode can comprise an affinity property. A spatial label can comprise an affinity property. An affinity property can be include a chemical and/or biological moiety that can facilitate binding of the stochastic barcode to another entity (e.g., cell receptor). For example, an affinity property can comprise an antibody. An antibody can be specific for a specific moiety (e.g., receptor) on a sample. An antibody can guide the stochastic barcode to a specific cell type or molecule. Targets at and/or near the specific cell type or molecule can be stochastically labeled. An affinity property can also provide spatial information in addition to the nucleotide sequence of the spatial label because the antibody can guide the stochastic barcode to a specific location. An antibody can be a therapeutic antibody. An antibody can be a monoclonal antibody. An antibody can be a polyclonal antibody. An antibody can be humanized. An antibody can be chimeric. An antibody can be a naked antibody. An antibody can be a fusion antibody.

An antibody, can refer to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody can be an antibody fragment. An antibody fragment can be a portion of an antibody such as F(ab')2, Fab', Fab, Fv, sFv and the like. An antibody fragment can bind with the same antigen that is recognized by the full-length antibody. An antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for antibodies for cancer cells, antibodies for viruses, antibodies that bind to cell surface receptors (CD8, CD34, CD45), and therapeutic antibodies.

The cellular label and/or any label of the disclosure may further comprise a unique set of nucleic acid sub-sequences of defined length, e.g. 7 nucleotides each (equivalent to the number of bits used in some Hamming error correction codes), which are designed to provide error correction capability. The set of error correction sub-sequences comprise 7 nucleotide sequences can be designed such that any pairwise combination of sequences in the set exhibits a defined "genetic distance" (or number of mismatched bases), for example, a set of error correction sub-sequences may be designed to exhibit a genetic distance of 3 nucleotides. In some embodiments, the length of the nucleic acid sub-sequences used for creating error correction codes may vary, for example, they may be at least 3 nucleotides, at least 7 nucleotides, at least 15 nucleotides, or at least 31 nucleotides in length. In some embodiments, nucleic acid sub-sequences of other lengths may be used for creating error correction codes.

Stochastic barcodes of the disclosure can comprise error-correcting sequences (e.g., Hamming codes) in them for error-correction. A Hamming code can refer an arithmetic process that identifies unique binary codes based upon inherent redundancy that are capable of correcting single bit errors. For example, a Hamming code can be matched with a nucleic acid barcode in order to screen for single nucleotide errors occurring during nucleic acid amplification. The identification of a single nucleotide error by using a Hamming code, thereby can allow for the correction of the nucleic acid barcode.

When a stochastic barcode comprises more than one of a type of label (e.g., more than one cellular label or more than one molecular label), the labels may be interspersed with a linker label sequence. A linker label sequence may be at least about 5, 10, 15, 20, 25, 30, 35, 40, 45, 50 or more nucleotides in length. A linker label sequence may be at most about 5, 10, 15, 20, 25, 30, 35, 40, 45, 50 or more nucleotides in length. In some instances, a linker label sequence is 12 nucleotides in length. A linker label sequence may be used to facilitate the synthesis of the stochastic barcode. The linker label can comprise an error-correcting (e.g., Hamming) code.

Solid Supports

The stochastic barcodes disclosed herein may be attached to a solid support (e.g., bead, substrate). As used herein, the terms "tethered", "attached", and "immobilized" are used interchangeably, and may refer to covalent or non-covalent means for attaching stochastic barcodes to a solid support. Any of a variety of different solid supports may be used as solid supports for attaching pre-synthesized stochastic barcodes or for in situ solid-phase synthesis of stochastic barcode.

In some instances, a solid support is a bead. A bead may encompass any type of solid, porous, or hollow sphere, ball, bearing, cylinder, or other similar configuration composed of plastic, ceramic, metal, or polymeric material onto which a nucleic acid may be immobilized (e.g., covalently or non-covalently). A bead may comprise a discrete particle that may be spherical (e.g., microspheres) or have a non-spherical or irregular shape, such as cubic, cuboid, pyramidal, cylindrical, conical, oblong, or disc-shaped, and the like. A bead may be non-spherical in shape.

Beads may comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, sepharose, agarose, hydrogel, polymer, cellulose, nylon, and any combination thereof.

The diameter of the beads can vary, for example may be at least about 5 µm, 10 µm, 20 µm, 25 µm, 30 µm, 35 µm, 40 µm, 45 µm or 50 µm. The diameter of the beads may be at most about 5 µm, 10 µm, 20 µm, 25 µm, 30 µm, 35 µm, 40 µm, 45 µm or 50 µm. The diameter of the bead may be related to the diameter of the wells of the substrate. For example, the diameter of the bead may be at least 10, 20, 30, 40, 50, 60, 70, 80, 90 or 100% longer or shorter than the diameter of the well. The diameter of the bead may be at most 10, 20, 30, 40, 50, 60, 70, 80, 90 or 100% longer or shorter than the diameter of the well. The diameter of the bead may be related to the diameter of a cell (e.g., a single cell entrapped by the a well of the substrate). The diameter of the bead may be at least 10, 20, 30, 40, 50, 60, 70, 80, 90, 100, 150, 200, 250, or 300% or more longer or shorter than the diameter of the cell. The diameter of the bead may be at most 10, 20, 30, 40, 50, 60, 70, 80, 90, 100, 150, 200, 250, or 300% or more longer or shorter than the diameter of the cell.

A bead may be attached to and/or embedded in a substrate of the disclosure. A bead may be attached to and/or embedded in a gel, hydrogel, polymer and/or matrix. The spatial position of a bead within a substrate (e.g., gel, matrix, scaffold, or polymer) may be identified using the spatial label present on the stochastic barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligodT conjugated beads, silica beads, silica-like beads, anti-biotin microbead, anti-fluorochrome microbead, and BcMag™ Carboxy-Terminated Magnetic Beads.

A bead may be associated with (e.g. impregnated with) quantum dots or fluorescent dyes to make it fluorescent in one fluorescence optical channel or multiple optical channels. A bead may be associated with iron oxide or chromium oxide to make it paramagnetic or ferromagnetic. Beads can be identifiable. A bead can be imaged using a camera. A bead can have a detectable code associated with the bead. For example, a bead can comprise an RFID tag. A bead can comprise any detectable tag (e.g., UPC code, electronic barcode, etched identifier). A bead can change size, for example due to swelling in an organic or inorganic solution. A bead can be hydrophobic. A bead can be hydrophilic. A bead can be biocompatible.

A solid support (e.g., bead) can be visualized. The solid support can comprise a visualizing tag (e.g., fluorescent dye). A solid support (e.g., bead) can be etched with an identifier (e.g., a number). The identifier can be visualized through imaging the solid supports (e.g., beads).

A solid support may refer to an insoluble, semi-soluble, or insoluble material. A solid support may be referred to as "functionalized" when it includes a linker, a scaffold, a building block, or other reactive moiety attached thereto, whereas a solid support may be "nonfunctionalized" when it lack such a reactive moiety attached thereto. The solid support may be employed free in solution, such as in a microtiter well format; in a flow-through format, such as in a column; or in a dipstick.

The solid support may comprise a membrane, paper, plastic, coated surface, flat surface, glass, slide, chip, or any combination thereof. A solid support may take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

A solid support can be, in some embodiments, a biological molecule. For example, a solid support can be a nucleic acid, a protein, an antibody, a histone, a cellular compartment, a lipid, a carbohydrate, and the like. Solid supports that are biological molecules can be amplified, translated, transcribed, degraded, and/or modified (e.g., pegylated, sumoylated, acetylated, methylated). A solid support that is a biological molecule can provide spatial and time information in addition to the spatial label that is attached to the biological molecule. For example, a biological molecule can comprise a first confirmation when unmodified, but can change to a second confirmation when modified. The different conformations can expose stochastic barcodes of the disclosure to targets. For example, a biological molecule can comprise stochastic barcodes that are unaccessible due to folding of the biological molecule. Upon modification of the biological molecule (e.g., acetylation), the biological molecule can change conformation to expose the stochastic labels. The timing of the modification can provide another time dimension to the method of stochastic barcoding of the disclosure.

In another example, the biological molecule comprising stochastic barcodes of the disclosure can be located in the cytoplasm of a cell. Upon activation, the biological molecule can move to the nucleus, whereupon stochastic barcoding can take place. In this way, modification of the biological molecule can encode additional space-time information for the targets identified by the stochastic barcodes.

A dimension label can provide information about space-time of a biological event (e.g., cell division). For example, a dimension label can be added to a first cell, the first cell can divide generating a second daughter cell, the second daughter cell can comprise all, some or none of the dimension labels. The dimension labels can be activated in the original cell and the daughter cell. In this way, the dimension label can provide information about time of stochastic barcoded in distinct spaces.

Samples

As described herein, the plurality of nucleic acid molecules can be obtained or derived from a sample, for example a cell sample. A sample for use in the method of the disclosure can comprise one or more cells. A sample can refer to one or more cells. In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some instances, the cells are derived from a cancer but collected from a bodily fluid (e.g. circulating tumor cells). Non-limiting examples of cancers may include, adenoma, adenocarcinoma, squamous cell carcinoma, basal cell carcinoma, small cell carcinoma, large cell undifferentiated carcinoma, chondrosarcoma, and fibrosarcoma.

In some embodiments, the cells are cells that have been infected with virus and contain viral oligonucleotides. In some embodiments, the viral infection may be caused by a virus selected from the group consisting of double-stranded DNA viruses (e.g. adenoviruses, herpes viruses, pox viruses), single-stranded (+ strand or "sense") DNA viruses (e.g. parvoviruses), double-stranded RNA viruses (e.g. reoviruses), single-stranded (+ strand or sense) RNA viruses (e.g. picornaviruses, togaviruses), single-stranded (− strand or antisense) RNA viruses (e.g. orthomyxoviruses, rhabdoviruses), single-stranded ((+ strand or sense) RNA viruses with a DNA intermediate in their life-cycle) RNA-RT viruses (e.g. retroviruses), and double-stranded DNA-RT viruses (e.g. hepadnaviruses). Exemplary viruses can include, but are not limited to, SARS, HIV, coronaviruses, Ebola, Malaria, Dengue, Hepatitis C, Hepatitis B, and Influenza.

In some embodiments, the cells are bacteria. These may include either gram-positive or gram-negative bacteria. Examples of bacteria that may be analyzed using the disclosed methods, devices, and systems include, but are not limited to, *Actinomedurae, Actinomyces israelii, Bacillus anthracia, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like. Gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like. Other bacteria may include *Myobacterium avium, Myobacterium leprae, Myobacterium tuberculosis, Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum,*

*Diplococcus pneumoniae, Ehrlichia chafensis, Enterococcus faecium*, Meningococci and the like.

In some embodiments, the cells are fungi. Non-limiting examples of fungi that may be analyzed using the disclosed methods, devices, and systems include, but are not limited to, Aspergilli, Candidae, *Candida albicans, Coccidioides immitis*, Cryptococci, and combinations thereof.

In some embodiments, the cells are protozoans or other parasites. Examples of parasites to be analyzed using the methods, devices, and systems of the present disclosure include, but are not limited to, *Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii, Trypanosomae*, trapezoidal amoeba, worms (e.g., helminthes), particularly parasitic worms including, but not limited to, Nematoda (roundworms, e.g., whipworms, hookworms, pinworms, ascarids, filarids and the like), Cestoda (e.g., tapeworms).

As used herein, the term "cell" can refer to one or more cells. In some embodiments, the cells are normal cells, for example, human cells in different stages of development, or human cells from different organs or tissue types (e.g. white blood cells, red blood cells, platelets, epithelial cells, endothelial cells, neurons, glial cells, fibroblasts, skeletal muscle cells, smooth muscle cells, gametes, or cells from the heart, lungs, brain, liver, kidney, spleen, pancreas, thymus, bladder, stomach, colon, small intestine). In some embodiments, the cells may be undifferentiated human stem cells, or human stem cells that have been induced to differentiate. In some embodiments, the cells may be fetal human cells. The fetal human cells may be obtained from a mother pregnant with the fetus. In some embodiments, the cells are rare cells. A rare cell may be, for example, a circulating tumor cell (CTC), circulating epithelial cell, circulating endothelial cell, circulating endometrial cell, circulating stem cell, stem cell, undifferentiated stem cell, cancer stem cell, bone marrow cell, progenitor cell, foam cell, mesenchymal cell, trophoblast, immune system cell (host or graft), cellular fragment, cellular organelle (e.g. mitochondria or nuclei), pathogen infected cell, and the like.

In some embodiments, the cells are non-human cells, for example, other types of mammalian cells (e.g. mouse, rat, pig, dog, cow, or horse). In some embodiments, the cells are other types of animal or plant cells. In other embodiments, the cells may be any prokaryotic or eukaryotic cells.

In some embodiments, a first cell sample is obtained from a person not having a disease or condition, and a second cell sample is obtained from a person having the disease or condition. In some embodiments, the persons are different. In some embodiments, the persons are the same but cell samples are taken at different time points. In some embodiments, the persons are patients, and the cell samples are patient samples. The disease or condition can be a cancer, a bacterial infection, a viral infection, an inflammatory disease, a neurodegenerative disease, a fungal disease, a parasitic disease, a genetic disorder, or any combination thereof.

In some embodiments, cells suitable for use in the presently disclosed methods may range in size from about 2 micrometers to about 100 micrometers in diameter. In some embodiments, the cells may have diameters of at least 2 micrometers, at least 5 micrometers, at least 10 micrometers, at least 15 micrometers, at least 20 micrometers, at least 30 micrometers, at least 40 micrometers, at least 50 micrometers, at least 60 micrometers, at least 70 micrometers, at least 80 micrometers, at least 90 micrometers, or at least 100 micrometers. In some embodiments, the cells may have diameters of at most 100 micrometers, at most 90 micrometers, at most 80 micrometers, at most 70 micrometers, at most 60 micrometers, at most 50 micrometers, at most 40 micrometers, at most 30 micrometers, at most 20 micrometers, at most 15 micrometers, at most 10 micrometers, at most 5 micrometers, or at most 2 micrometers. The cells may have a diameter of any value within a range, for example from about 5 micrometers to about 85 micrometers. In some embodiments, the cells have diameters of about 10 micrometers.

In some embodiments the cells are sorted prior to associating a cell with a bead and/or in a microwell. For example the cells can be sorted by fluorescence-activated cell sorting or magnetic-activated cell sorting, or e.g., by flow cytometry. The cells may be filtered by size. In some instances a retentate contains the cells to be associated with the bead. In some instances the flow through contains the cells to be associated with the bead.

In some embodiments, the sample comprises an immune cell. An immune cell can include, for example, T cell, B cell, lymphoid stem cell, myeloid progenitor cell, lymphocyte, granulocyte, B-cell progenitor, T cell progenitor, Natural Killer cell, Tc cell, Th cell, plasma cell, memory cell, neutrophil, eosinophil, basophil, mast cell, monocyte, dendritic cell and/or macrophage, or any combination thereof.

A T cell can be a T cell clone, which can refer to T cells derived from a single T cell or those having identical TCRs. A T cell can be part of a T cell line which can include T cell clones and mixed populations of T cells with different TCRs all of which may recognize the same target (e.g., antigen, tumor, virus). T cells can be obtained from a number of sources, including peripheral blood mononuclear cells, bone marrow, lymph node tissue, spleen tissue, and tumors. T cells can be obtained from a unit of blood collected from a subject, such as using the Ficoll separation. Cells from the circulating blood of an individual can be obtained by apheresis or leukapheresis. The apheresis product can comprise lymphocytes, including T cells, monocytes, granulocytes, B cells, other nucleated white blood cells, red blood cells, and platelets. The cells can be washed and resuspended in media to isolate the cell of interest.

T cells can be isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, T cells can be isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. Immune cells (e.g., T cells and B cells) can be antigen specific (e.g., specific for a tumor.

In some embodiments, the cell can be an antigen-presenting cell (APC), such as a B cell, an activated B cell from a lymph node, a lymphoblastoid cell, a resting B-cell, or a neoplastic B cell, e.g. from a lymphoma. An APC can refer to a B-cell or a follicular dendritic cell expressing at least one of the BCRC proteins on its surface.

Methods of Stochastic Barcoding and Library Normalization

The disclosure provides for methods for library normalization of a sample. Methods of library normalization can be combined with any library sample preparation method. Methods of library normalization can be combined with stochastic barcoding methods of the disclosure. Stochastic barcoding can be used to index individual nucleic acid molecules (e.g., mRNA molecules) with unique barcodes, such that molecules of specific targets can be tracked and/or counted.

Figure 2:
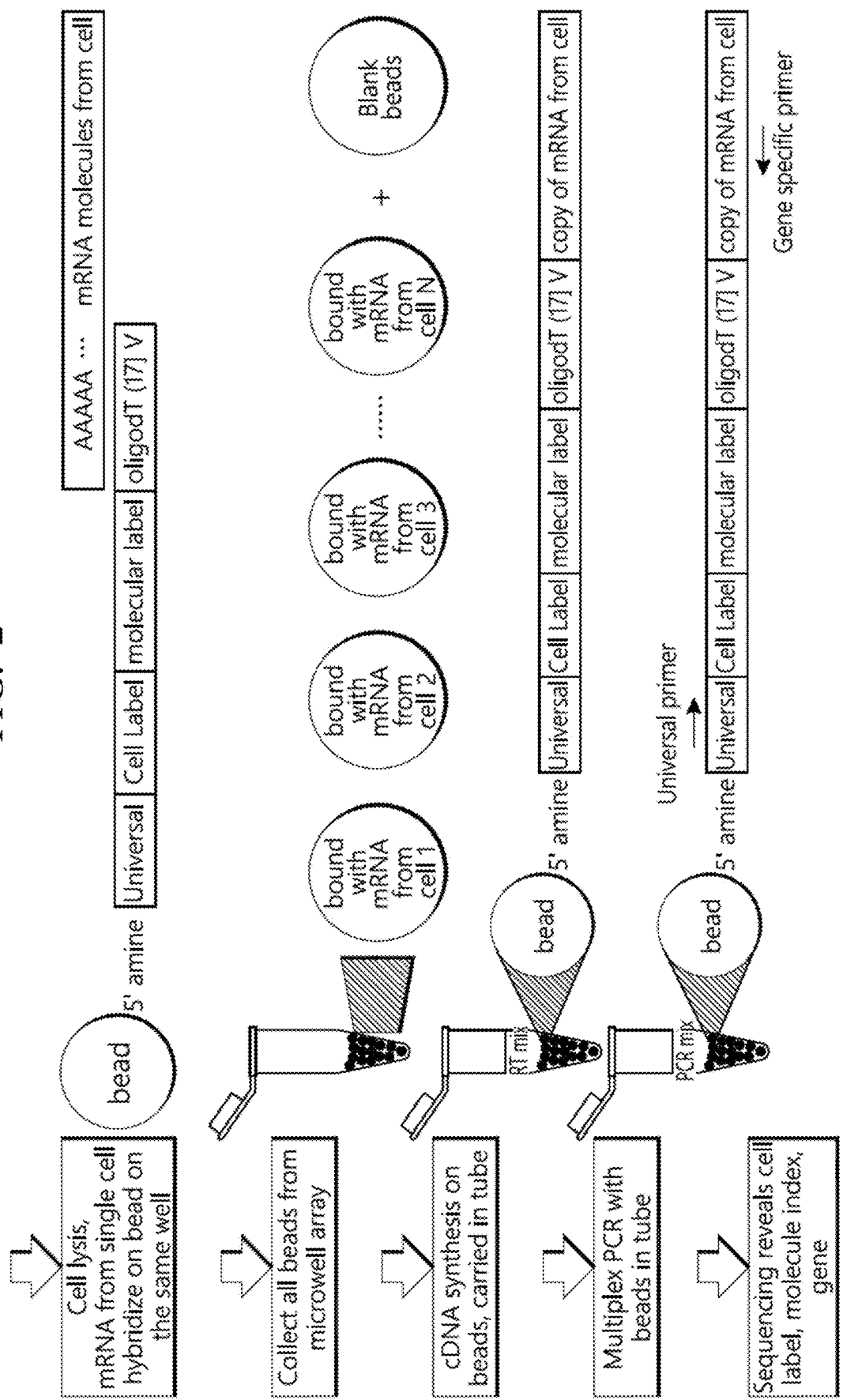
FIG. 2 illustrates an exemplary embodiment of the stochastic barcoding method of the disclosure.

The methods of stochastic barcoding can comprise placing the stochastic barcodes in close proximity with the sample, lysing the sample, associating distinct targets with the stochastic barcodes, amplifying the targets and/or digitally counting the targets. FIG. 2 illustrates an exemplary embodiment of the stochastic barcoding method of the disclosure. A sample (e.g., section of a sample, thin slice, and/or cell) can be contacted with a solid support comprising a stochastic barcode. Targets in the sample can be associated with the stochastic barcodes. The solid supports can be collected. cDNA synthesis can be performed on the solid support. cDNA synthesis can be performed off the solid support. cDNA synthesis can incorporate the label information from the labels in the stochastic barcode into the new cDNA target molecule being synthesized, thereby generating a target-barcode molecule. The target-barcode molecules can be amplified using PCR. The sequence of the targets and the labels of the stochastic barcode on the target-barcode molecule can be determined by sequencing methods.

Contacting a Sample and a Stochastic Barcode

A sample comprising, for example, a cell, organ, or tissue thin section, can be contacted to stochastic barcodes. The solid supports can be free floating. The solid supports can be embedded in a semi-solid or solid array. The stochastic barcodes may not be associated with solid supports. The stochastic barcodes may be individual nucleotides. The stochastic barcodes may be associated with a substrate. When stochastic barcodes are in close proximity to targets, the targets can hybridize to the stochastic barcode. The stochastic barcodes can be contacted at a non-depleatable ratio such that each distinct target can associate with a distinct stochastic barcode of the disclosure. To ensure efficient association between the target and the stochastic barcode, the targets can be crosslinked to the stochastic barcode.

The probability that two distinct targets of a sample can contact the same unique stochastic barcode can be at least $10^{-6}$, $10^{-5}$, $10^{-4}$, $10^{-3}$, $10^{-2}$, or $10^{-1}$ or more. The probability that two distinct targets of a sample can contact the same unique stochastic barcode can be at most $10^{-6}$, $10^{-5}$, $10^{-4}$, $10^{-3}$, $10^{-2}$, or $10^{-1}$ or more. The probability that two targets of the same same gene from the same cell can contact the same stochastic barcode can be at least $10^{-6}$, $10^{-5}$, $10^{-4}$, $10^{-3}$, $10^{-2}$, or $10^{-1}$ or more. The probability that two targets of the same gene from the same cell can contact the same stochastic barcode can be at most $10^{-6}$, $10^{-5}$, $10^{-4}$, $10^{-3}$, $10^{-2}$, or $10^{-1}$ or more.

In some instances, cells from a population of cells can be separated (e.g., isolated) into wells of a substrate of the disclosure. The population of cells can be diluted prior to separating. The population of cells can be diluted such that at least 1, 5, 10, 15, 20, 25, 30, 35, 40, 45, 50, 55, 60, 65, 70, 75, 80, 85, 90, 95 or 100% of wells of the substrate receive a single cell. The population of cells can be diluted such that at most 1, 5, 10, 15, 20, 25, 30, 35, 40, 45, 50, 55, 60, 65, 70, 75, 80, 85, 90, 95 or 100% of wells of the substrate receive a single cell. The population of cells can be diluted such that the number of cells in the diluted population is at least 1, 5, 10, 15, 20, 25, 30, 35, 40, 45, 50, 55, 60, 65, 70, 75, 80, 85, 90, 95 or 100% of the number of wells on the substrate. The population of cells can be diluted such that the number of cells in the diluted population is at least 1, 5, 10, 15, 20, 25, 30, 35, 40, 45, 50, 55, 60, 65, 70, 75, 80, 85, 90, 95 or 100% of the number of wells on the substrate.

In some instances, the population of cells is diluted such that the number of cell is about 10% of the number of wells in the substrate.

Distribution of single cells into wells of the substrate can follow a Poisson distribution. For example, there can be at least a 0.1, 0.5, 1, 2, 3, 4, 5, 6, 7, 8, 9 or 10% or more probability that a well of the substrate has more than one cell. There can be at least a 0.1, 0.5, 1, 2, 3, 4, 5, 6, 7, 8, 9 or 10% or more probability that a well of the substrate has more than one cell. Distribution of single cells into wells of the substrate can be random. Distribution of single cells into wells of the substrate can be non-random. The cells can be separated such that a well of the substrate receives only one cell.

Cell Lysis

Following the distribution of cells and stochastic barcodes, the cells can be lysed to liberate the target molecules. Cell lysis may be accomplished by any of a variety of means, for example, by chemical or biochemical means, by osmotic shock, or by means of thermal lysis, mechanical lysis, or optical lysis. Cells may be lysed by addition of a cell lysis buffer comprising a detergent (e.g. SDS, Li dodecyl sulfate, Triton X-100, Tween-20, or NP-40), an organic solvent (e.g. methanol or acetone), or digestive enzymes (e.g. proteinase K, pepsin, or trypsin), or any combination thereof. To increase the association of a target and a stochastic barcode, the rate of the diffusion of the target molecules can be altered by for example, reducing the temperature and/or increasing the viscosity of the lysate.

Attachment of Stochastic Barcodes to Target Nucleic Acid Molecules

Following lysis of the cells and release of nucleic acid molecules therefrom, the nucleic acid molecules may randomly associate with the stochastic barcodes of the co-localized solid support. Association may comprise hybridization of a stochastic barcode's target recognition region to a complementary portion of the target nucleic acid molecule (e.g., oligo dT of the stochastic barcode can interact with a poly-A tail of a target). The assay conditions used for hybridization (e.g. buffer pH, ionic strength, temperature, etc.) can be chosen to promote formation of specific, stable hybrids.

Attachment may further comprise ligation of a stochastic barcode's target recognition region and a portion of the target nucleic acid molecule. For example, the target binding region may comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The stochastic barcode may then be ligated to any nucleic acid molecule comprising a sequence complementary to the restriction site overhang. A ligase (e.g., T4 DNA ligase) may be used to join the two fragments.

The labeled targets from a plurality of cells (or a plurality of samples) (e.g., target-barcode molecules) can be subsequently pooled, for example by retrieving the stochastic barcodes and/or the beads to which the target-barcode molecules are attached. The retrieval of solid support-based collections of attached target-barcode molecules may be implemented by use of magnetic beads and an externally-applied magnetic field. Once the target-barcode molecules have been pooled, all further processing may proceed in a single reaction vessel. Further processing can include, for example, reverse transcription reactions, amplification reactions, cleavage reactions, dissociation reactions, and/or nucleic acid extension reactions. Further processing reactions may be performed within the microwells, that is, without first pooling the labeled target nucleic acid molecules from a plurality of cells.

Reverse Transcription

The disclosure provides for a method to create a stochastic target-barcode conjugate using reverse transcription. The stochastic target-barcode conjugate can comprise the stochastic barcode and a complementary sequence of all or a portion of the target nucleic acid (i.e. a stochastically barcoded cDNA molecule). Reverse transcription of the associated RNA molecule may occur by the addition of a reverse transcription primer along with the reverse transcriptase. The reverse transcription primer can be an oligo-dT primer, a random hexanucleotide primer, or a target-specific oligonucleotide primer. Oligo-dT primers can be, for example, 12-18 nucleotides in length and bind to the endogenous poly-A tail at the 3' end of mammalian mRNA. Random hexanucleotide primers may bind to mRNA at a variety of complementary sites. Target-specific oligonucleotide primers typically selectively prime the mRNA of interest.

The stochastically barcoded cDNA molecule can be subjected to downstream methods such as amplification (e.g., by universal and/or gene-specific primers) and the library normalization methods of the disclosure.

Kits

Disclosed herein are kits for performing library normalization methods of the disclosure. A kit can comprise a second strand synthesis primer comprising a binding moiety. A kit can comprise a solid support comprising capture moieties that can bind to the binding moiety on the second strand synthesis primer. A kit can comprise a magnet to capture the solid support. A kit can comprise reagents for cleaning up an amplification reaction (e.g., AmpureXP beads and/or a purification spin column). A kit can comprise adaptors and/or primers comprising sequencing flow cell sequences. The kit may further comprise reagents (e.g. enzymes, primers, dNTPs, NTPs, RNAse inhibitors, or buffers) for performing nucleic acid extension reactions, for example, reverse transcription reactions and primer extension reactions. The kit may further comprise reagents (e.g. enzymes, universal primers, sequencing primers, target-specific primers, or buffers) for performing amplification reactions to prepare sequencing libraries.

Disclosed herein are kits for performing stochastic barcoding assays. The kits can comprise one or more solid support suspensions, wherein the individual solid supports within a suspension comprise a plurality of attached stochastic barcodes of the disclosure. The kits can comprise stochastic barcodes that may not be attached to a solid support. The kit may further comprise reagents, e.g. lysis buffers, rinse buffers, or hybridization buffers, for performing the stochastic barcoding assay. The kit may further comprise reagents (e.g. enzymes, primers, dNTPs, NTPs, RNAse inhibitors, or buffers) for performing nucleic acid extension reactions, for example, reverse transcription reactions and primer extension reactions. The kit may further comprise reagents (e.g. enzymes, universal primers, sequencing primers, target-specific primers, or buffers) for performing amplification reactions to prepare sequencing libraries.

Kits of the disclosure can generally include instructions for carrying out one or more of the methods described herein. Instructions included in kits can be affixed to packaging material or can be included as a package insert. While the instructions are typically written or printed materials they are not limited to such. Any medium capable of storing such instructions and communicating them to an end user is contemplated by the disclosure. Such media can include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Library Normalization with Nested PCR

This example provides for methods for library normalization with nested PCR. A plurality of mRNAs are reverse transcribed into a plurality of cDNAs using a primer comprising an oligo dT sequence, a molecular label, a sample label, and a universal label. The cDNAs are amplified in a first amplification reaction using a gene-specific reverse primer and a universal primer (e.g., that binds to the universal label), thereby generating a first set of amplicons. The universal primer can comprise a biotin moiety. The first set of amplicons can be amplified in a second amplification reaction using a second gene-specific nested PCR primer and the universal primer comprising the biotin moiety. This reaction generates an asymmetrically labeled amplicon comprising a biotin moiety at one end. The library is heat denatured. The library is cooled to induce partial re-annealing. During partial re-annealing, highly abundant amplicons will re-anneal faster than lower abundant amplicons.

The partially re-annealed library can be contacted with a solid support comprising streptavidin moieties. The streptavidin can bind to the biotin moieties on the strands of the library. Re-annealed amplicons will comprise the biotin and will be removed by the streptavidin. Strands that have not re-annealed that comprise the biotin will also be removed by the streptavidin. The remaining strands represent sequences that are lower in abundance and are the complement of the strands with the biotin. These strands represent a normalized library.

The library is regenerated with PCR primers. The PCR primers can comprise sequencing flow cell primer sequences. The normalized library is sequenced.

Example 2: Library Normalization with Whole Transcriptome Amplification

Library normalization can be performed on a library generated from whole transcriptome amplification. Whole transcriptome amplification can be performed using an adaptor ligation method. A target comprises a poly-A tail. The target is an mRNA. The target is hybridized to a stochastic barcode. The stochastic barcode comprises a number of labels. For example, the stochastic barcode comprises a target-specific region (e.g., oligo dT for binding to poly-A tails of mRNAs), a molecular label, a cellular label, and a first universal label. The stochastic barcode is reverse transcribed using a reverse transcriptase, thereby generating a labelled-cDNA molecule. Excess stochastic barcodes are treated with a degradation enzyme. The degradation enzyme is an exonuclease.

The labelled-cDNA molecule undergoes second strand synthesis thereby generating a double-stranded labeled cDNA molecule. Second strand synthesis is performed by contacting the labelled cDNA molecule-mRNA hybrid with a nicking enzyme (e.g., RNaseH) that can nick the mRNA hybridized to the labelled cDNA molecule, thereby generating nicked mRNA. The nicked mRNA is used as a primer and extended using a polymerase (e.g., DNA Pol I), thereby incorporating the sequence of the first strand. The polymerase comprises 5'-3' exonuclease activity. The polymerase degrades the downstream mRNA nicks that serve as the primers for the second strand synthesis. A ligase is used to ligate the extended sequences together, thereby generating a second strand (e.g., double-stranded labeled cDNA molecule).

The double-stranded labeled cDNA molecule comprises a sequence that is complementary to the first universal label. The double-stranded labeled cDNA molecule is contacted with an adaptor. The adaptor is double-stranded. The adaptor comprises a restriction endonuclease cleavage site. The adaptor comprises a second universal primer sequence (that is the same as the first one). The adaptor comprises a 3' overhang. The adaptor comprises a free 5' phosphate (P) which can ligate to the 3' hydroxyl of the double-stranded labelled-cDNA molecule. The adaptor ligates to both strands of the double-stranded labelled cDNA molecule 1558.

The product is amplified using one or more WTA amplification primers. One of the WTA amplification primers comprises a biotin moiety. One of the WTA amplification primers does not comprise a biotin moiety. The product is amplified such that one strand is linearly amplified and one strand is exponentially amplified. The linearly amplified strand comprises the amplifiable universal sequence at one end. The exponentially amplifiable strand comprises universal sequences at both ends, with one of the ends comprising a biotin moiety. The WTA amplified product is subjected to the library normalization protocol as described in Example 1.

Example 3: Use of Blockers in Library Normalization

This example provides for methods for library normalization with blockers. A plurality of mRNAs are reverse transcribed into a plurality of cDNAs using a primer comprising an oligo dT sequence, a molecular label, a sample label, and a universal label. The cDNAs are amplified in a first amplification reaction using a gene-specific reverse primer and a universal primer (e.g., that binds to the universal label), thereby generating a first set of amplicons. The universal primer can comprise a biotin moiety. The first set of amplicons are amplified in a second amplification reaction using a second gene-specific nested PCR primer and the universal primer comprising the biotin moiety. This reaction generates an asymmetrically labeled amplicon comprising a biotin moiety at one end. Blockers are added to the library. The library is heat denatured. The blockers bind to the universal labels of the amplicons. The library is cooled to induce partial re-annealing. During partial re-annealing, highly abundant amplicons will re-anneal faster than lower abundant amplicons. Partial re-annealing will be driven more by the target sequences than by any of the sequences in the primer (e.g., molecular, sample, universal label).

The partially re-annealed library is contacted with a solid support comprising streptavidin moieties. The streptavidin can bind to the biotin moieties on the strands of the library. Re-annealed amplicons will comprise the biotin and will be removed by the streptavidin. Strands that have not re-annealed that comprise the biotin will also be removed by the streptavidin. The remaining strands represent sequences that are lower in abundance and are the complement of the strands with the biotin. These strands represent a normalized library.

The library is regenerated with PCR primers. The PCR primers can comprise sequencing flow cell primer sequences. The normalized library is sequenced.

Example 4: Library Normalization on a Solid Support

This example provides for methods for library normalization with a solid support. A plurality of mRNAs are reverse transcribed into a plurality of cDNAs using a primer comprising an oligo dT sequence, a molecular label, a sample label, and a universal label. The cDNAs are amplified in a first amplification reaction using a gene-specific reverse primer and a universal primer (e.g., that binds to the universal label), thereby generating a first set of amplicons. The universal primer can comprise an azide or alkyne moiety. The first set of amplicons can be amplified in a second amplification reaction using a second gene-specific nested PCR primer and the universal primer comprising the azide or alkyne moiety. This reaction generates an asymmetrically labeled amplicon comprising an azide or alkyne moiety at one end.

The library is attached to a solid support using click chemistry. The solid support comprises a complementary molecule involved in click chemistry. For example, if the amplicon comprises an alkyne, then the solid support comprises an azide. The library is heat denatured. In some instances, blockers are introduced. The library is cooled to induce partial re-annealing. During partial re-annealing, highly abundant amplicons will re-anneal faster than lower abundant amplicons.

Re-annealed amplicons will be attached to the solid support through the click chemistry. The solid support is removed (e.g., by centrifugation or magnetism). The remaining strands (e.g., that have not re-annealed) will not comprise an azide or alkyne moiety. The remaining strands represent sequences that are lower in abundance and are the complement of the strands with the azide or alkyne. These strands represent a normalized library.

The library is regenerated with PCR primers. The PCR primers can comprise sequencing flow cell primer sequences. The normalized library is sequenced.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

What is claimed is:

1. A method of reducing the content of high abundance species from a first plurality of nucleic acid molecules, comprising:

hybridizing a plurality of first oligonucleotides comprising a binding moiety with a first plurality of nucleic acid molecules, thereby forming hybridization complexes comprising the plurality of first oligonucleotides, wherein the first plurality of nucleic acid molecules comprises at least one high abundance species and at least one low abundance species, wherein the binding moiety comprises a functional group attached to the first oligonucleotides, wherein the first plurality of nucleic acid molecules are mRNAs;

extending the plurality of first oligonucleotides of the hybridization complexes, thereby generating a plurality of double-stranded nucleic acid molecules comprising (i) a plurality of complementary strands of the first plurality of nucleic acid molecules comprising the binding moiety and (ii) the first plurality of nucleic acid molecules;

denaturing the plurality of double-stranded nucleic acid molecules, thereby forming a denatured mixture;

forming an annealing mixture by partially reannealing the denatured mixture in a condition such that reannealed double stranded nucleic acids are generated in the annealing mixture, wherein the reannealed double stranded nucleic acids comprise the plurality of complementary strands of the first plurality of nucleic acid molecules, the at least one high abundance species, the at least one low abundance species, and the binding moiety, and the reannealed double stranded nucleic acids contain more amounts of the at least one high abundance species than the amounts of the at least one low abundance species; and removing the reannealed double stranded nucleic acids from the annealing mixture by a capture molecule immobilized on one or more solid support, thereby generating a second plurality of nucleic acid molecules and reducing the content of the high abundance species from the first plurality of nucleic acid molecules, wherein the capture molecules specifically bind to the binding moiety and the content of the at least one high abundance species in the second plurality of nucleic acid molecules is reduced in comparison to the content of the at least one high abundance species in the first plurality of nucleic acid molecules.

2. The method of claim 1, wherein the binding moiety is a functional group selected from the group consisting of biotin, streptavidin, heparin, an aptamer, a click-chemistry moiety, digoxigenin, primary amine(s), carboxyl(s), hydroxyl(s), aldehyde(s), ketone(s), and any combination thereof.

3. The method of claim 1, further comprising synthesizing a complementary strand of at least one of the plurality of complementary strands of the first plurality of nucleic acid molecules.

4. The method of claim 3, wherein the synthesizing step comprises hybridizing a plurality of second oligonucleotides to the plurality of complementary strands of the first plurality of nucleic acid molecules and extending the plurality of second oligonucleotides.

5. The method of claim 4, wherein the plurality of first oligonucleotides or the plurality of second oligonucleotides comprises a universal primer binding site.

6. The method of claim 1, further comprising amplifying the plurality of double-stranded nucleic acid molecules.

7. The method of claim 1, wherein the at least one high abundance species represents at least 50% of the first plurality of nucleic acid molecules.

8. The method of claim 1, further comprising sequencing the second plurality of nucleic acid molecules to generate a plurality of sequencing reads.

9. The method of claim 1, further comprising adding a plurality of blockers during the partially reannealing step.

10. The method of claim 9, wherein the plurality of first oligonucleotides comprises a universal primer binding site and the plurality of blockers hybridizes to the universal primer binding site of the plurality of first oligonucleotides.

11. The method of claim 10, wherein the plurality of blockers prevents hybridization between the universal primer binding site of the plurality of first oligonucleotides and its complementary sequence.

12. The method of claim 1, wherein the first plurality of nucleic acid molecules is a part of a genomic library.

13. The method of claim 1, wherein the first plurality of nucleic acid molecules is a part of a single-cell nucleic acid library.

14. A method of generating a normalized nucleic acid library, comprising:
hybridizing a plurality of first oligonucleotides comprising a binding moiety with a plurality of nucleic acid targets in an unnormalized nucleic acid library, thereby forming hybridization complexes comprising the plurality of first oligonucleotides, wherein the binding moiety comprises a functional group attached to the plurality of first oligonucleotides, wherein the plurality of nucleic acid targets comprise one or more high abundance nucleic acid targets and one or more low abundance nucleic acid targets, and wherein the plurality of nucleic acid targets are mRNAs;
extending the plurality of first oligonucleotides of the hybridization complexes, thereby generating a plurality of double-stranded nucleic acid molecules comprising (i) a plurality of complementary strands of the plurality of nucleic acid targets comprising the binding moiety and (ii) the plurality of nucleic acid targets;
denaturing the plurality of double-stranded nucleic acid molecules, thereby forming a denatured mixture;
forming an annealing mixture by partially reannealing the denatured mixture in a condition such that reannealed double stranded nucleic acids are generated in the annealed mixture, wherein the reannealed double stranded nucleic acids comprise the plurality of complementary strands of the plurality of nucleic acid targets, the one or more high abundance nucleic acid targets, the one or more low abundance nucleic acid targets, and the binding moiety, and the reannealed double stranded nucleic acids contain more amounts of the one or more high abundance nucleic acid targets than the amounts of the one or more low abundance nucleic acid targets; and
removing the reannealed double stranded nucleic acids from annealing mixture, thereby generating the normalized nucleic acid library.

15. The method of claim 14, wherein the binding moiety is a functional group selected from the group consisting of biotin, streptavidin, heparin, an aptamer, a click-chemistry moiety, digoxigenin, primary amine(s), carboxyl(s), hydroxyl(s), aldehyde(s), ketone(s), and any combination thereof.

16. The method of claim 14, further comprising synthesizing a complementary strand of one or more of the plurality of complementary strands of the plurality of nucleic acid targets.

17. The method of claim 16, wherein the synthesizing step comprises hybridizing a plurality of second oligonucleotides to the plurality of complementary strands of the plurality of nucleic acid targets and extending the plurality of second oligonucleotides.

18. The method of claim 17, wherein the plurality of first oligonucleotides or the plurality of second oligonucleotides comprises a universal primer binding site.

19. The method of claim 16, further comprising amplifying the plurality of double-stranded nucleic acid molecules.

20. The method of claim 14, further comprising sequencing the normalized nucleic acid library to generate a plurality of sequencing reads.

21. The method of claim 14, further comprising adding a plurality of blockers during the partially reannealing step.

22. The method of claim 21, wherein the plurality of first oligonucleotides comprises a universal primer binding site and the plurality of blockers hybridizes to the universal primer binding site of the plurality of first oligonucleotides.

23. The method of claim 22, wherein the plurality of blockers prevents hybridization between the universal primer binding site of the plurality of first oligonucleotides and its complementary sequence.

24. The method of claim 14, wherein the reannealed double stranded nucleic acids are removed by a capture molecule immobilized on one or more solid support, wherein the capture molecules specifically bind to the binding moiety.

25. The method of claim 14, wherein the plurality of first oligonucleotides comprises target-specific primers.

26. The method of claim 14, wherein the plurality of first oligonucleotides comprises non-target-specific primers.

27. The method of claim 14, wherein the plurality of nucleic acid targets is from a single cell.

* * * * *